United States Patent [19]

Suda et al.

[11] Patent Number: 4,731,855
[45] Date of Patent: Mar. 15, 1988

[54] PATTERN DEFECT INSPECTION APPARATUS

[75] Inventors: Kyo Suda, Hachioji; Shigeharu Kimura, Kokubunji; Shinobu Hase, Hachioji; Chusuke Munakata; Kanji Kinameri, both of Tokyo; Yoshitoshi Ito, Ome; Hiroto Nagatomo, Tokyo; Yuzo Taniguchi, Higashimurayama; Mikihito Saito, Tokyo, all of Japan

[73] Assignee: Hitachi, Ltd., Tokyo, Japan

[21] Appl. No.: 720,730

[22] Filed: Apr. 8, 1985

[30] Foreign Application Priority Data

Apr. 6, 1984 [JP] Japan ................................. 59-67640
May 1, 1984 [JP] Japan ................................. 59-86260
Sep. 10, 1984 [JP] Japan ............................... 59-187899

[51] Int. Cl.$^4$ ............................................. G06K 9/00
[52] U.S. Cl. ........................................ 382/8; 250/562; 356/237
[58] Field of Search ............... 382/8, 31, 57; 356/237, 356/354, 239; 388/101, 106; 250/562, 572, 550; 350/162.11

[56] References Cited

U.S. PATENT DOCUMENTS 3,790,280  2/1974  Heinz et al. ............................ 356/71
3,879,131  4/1975  Cuthbert et al. ..................... 356/354
3,905,019  9/1975  Aoki et al. ............................. 382/31
4,360,799  11/1982 Leighty et al. ....................... 382/31
4,377,340  3/1983  Green .................................... 250/562
4,428,672  1/1984  Allard et al. ......................... 356/237
4,578,810  3/1986  MacFarlane et al. .................. 382/8
4,598,997  7/1986  Steigmeier et al. ................. 356/237

Primary Examiner—Leo H. Boudreau
Assistant Examiner—Joseph Mancuso
Attorney, Agent, or Firm—Antonelli, Terry & Wands

[57] ABSTRACT

A pattern defect inspection apparatus detects presence or absence of a defect in a pattern formed on a semiconductor wafer by scanning the pattern normally to the surface thereof by a coherent light beam of a predetermined spot size, detecting reflected diffraction lights generated thereby and processing the detected lights. It comprises an abnormal direction signal detector including photo-detectors having wide light receiving areas arranged in a plurality of spatial areas which the reflected diffraction lights from a normal pattern do not normally reach, a normal pattern detector including photo-detectors having large light receiving areas arranged in a plurality of spatial areas which the reflected diffraction lights from the normal pattern reach, and a defect discriminator for determining if the abnormal direction signals are due to a true defect or not in accordance with the signals from the abnormal direction signal detector and the normal pattern detector.

13 Claims, 67 Drawing Figures

FIG. 10

| DIRECTION SYMBOL | NORMAL DIRECTION | PHOTO-DETECTORS * |
|---|---|---|
| I | 0° RELATIVE TO X-AXIS (X-AXIS) | 11-1 & 11-9 |
| II | 45° RELATIVE TO X-AXIS | 11-3 & 11-11 |
| III | 90° RELATIVE TO X-AXIS (NORMAL TO X-AXIS) | 11-5 & 11-13 |
| IV | 135° RELATIVE TO X-AXIS | 11-7 & 11-15 |

* SEE FIG. 8B

FIG. 11

| MAJOR CLASS | HIGH LEVEL SIGNALS GENERATED IN NORMAL DIRECTIONS | | | DIRECTIONS OF REFLECTED DIFFRACTION LIGHTS | BASIC PATTERNS |
|---|---|---|---|---|---|
| 1 | NONE | | | | BEAM SPOT, CIRCLE |
| 2 | ONE DIRECTION | | | III ↕ | EDGE, STRIPE, STRIPE WITH END (NARROW) |
| 3 | TWO DIRECTIONS | RIGHT ANGLE CORNER | RIGHT ANGLE CORNER | III ↕ ↔ I | (two right angle corner patterns) |
| | | | COMPOSITE RIGHT ANGLE CORNER | III ↕ ↔ I | T-SHAPE, U-SHAPE, +-SHAPE, STRIPE WITH END (WIDE), RECTANGLE, SQUARE |
| 4 | | OBLIQUE CROSSING | 135° CORNER | III ↖↘ II | 135° patterns |
| | | | 45° CORNER | IV ↙↗ III | 45° patterns |
| 5 | 5-1 | THREE DIRECTIONS | | III↑ ↗II →I | COMPOSITE PATTERN (1) (COMBINATION OF BASIC PATTERNS) |
| | 5-2 | FOUR DIRECTIONS | | IV↖ III↑ ↗II →I | COMPOSITE PATTERN (2) (COMBINATION OF BASIC PATTERN) |

FIG. 12

| MAJOR CLASS | HIGH LEVEL SIGNALS GENERATED IN NORMAL DIRECTIONS | | | NUMBER OF CASES | NORMAL DIRECTIONS OF REFLECTED DIFFRACTION LIGHTS | | | | PATTERNS |
|---|---|---|---|---|---|---|---|---|---|
| | | | | | I | II | III | IV | |
| 1 | NONE | | | 0 | (NOTE) | | | | |
| 2 | ONE DIRECTION | | | 4 | ↔ | | | | |
| | | | | | | ↗ | | | |
| | | | | | | | ↕ | | |
| | | | | | | | | ↘ | |
| 3 | TWO DIRECTIONS | RIGHT ANGLE CROSSING | RIGHT ANGLE PATTERN | 2 | ↔ | | ↕ | | |
| | | | | | | ↗ | | ↘ | |
| 4 | | OBLIQUE CROSSING | 45°,135° OBLIQUE CROSSING PATTERN | 4 | ↔ | ↗ | | | |
| | | | | | | ↗ | ↕ | | |
| | | | | | | | ↕ | ↘ | |
| | | | | | ↔ | | | ↘ | |
| 5 | THREE DIRECTIONS | | | 4 | ↔ | ↗ | ↕ | | |
| | | | | | | ↗ | ↕ | ↘ | |
| | | | | | ↔ | | ↕ | ↘ | |
| | | | | | ↔ | ↗ | | ↘ | |
| 6 | FOUR DIRECTIONS | | | 1 | ↔ | ↗ | ↕ | ↘ | |

NOTE: BLANK INDICATES NO SIGNAL GENERATED IN THAT DIRECTION

FIG. 13A
FIG. 13B
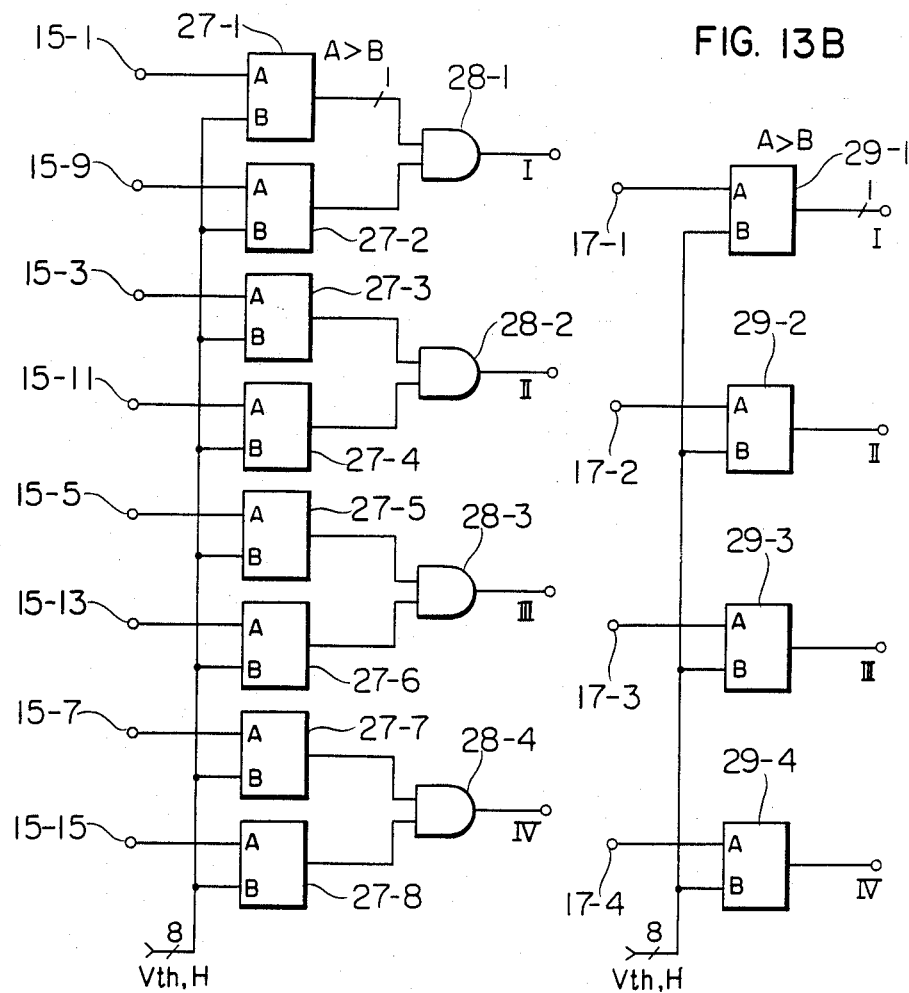
FIG. 14
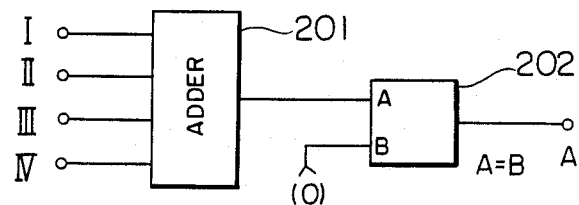

FIG. 19

| MAJOR CLASS | SUBCLASS | PATTERN TYPE | NUMBER OF DIRECTIONS | DIRECTIONS | | | | REMARK |
|---|---|---|---|---|---|---|---|---|
| | | | | I' | II' | III' | IV' | |
| 2 | i | SEMI-CIRCLE | 0 | | | | | |
| | ii | SEMI-CIRCLE | 3 | ↔ | ↗ | | ↘ | CIRCUIT IN FIG.15D |
| | | | | ↔ | ↗ | ↕ | | |
| | | | | | ↗ | ↕ | ↘ | |
| | | | | ↔ | | ↕ | ↘ | |
| 3 | i | QUARTER CIRCLE | 1 | ↔ | | | | |
| | | | | | | ↕ | | |
| | | | | | ↗ | | | |
| | | | | | | | ↘ | |
| | ii | QUARTER CIRCLE (2 OR 4) | 2 | | ↗ | | ↘ | CIRCUIT IN FIG.15B |
| | | | | ↔ | | ↕ | | |
| 4 | i | 1/8 CIRCLE | 0 | | | | | |
| | ii | 3/8 CIRCLE | 2 | ↔ | ↗ | | | CIRCUIT IN FIG.15C |
| | | | | | ↗ | ↕ | | |
| | | | | | | ↕ | ↘ | |
| | | | | ↔ | | | ↘ | |

FIG. 23
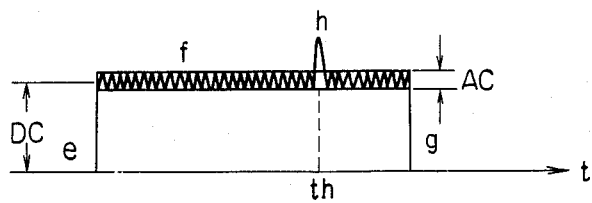
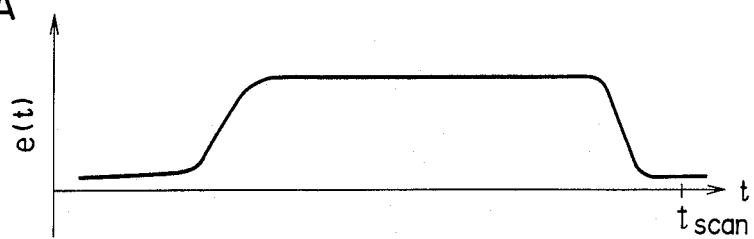
FIG. 24A
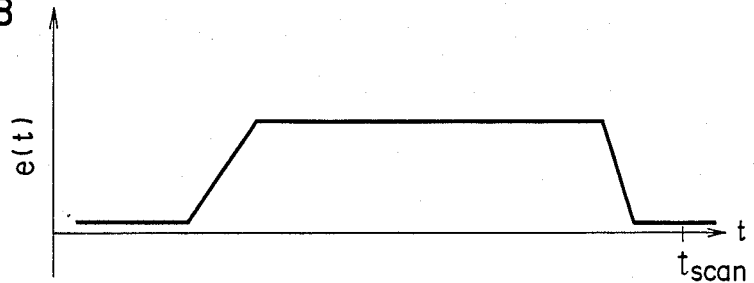
FIG. 24B
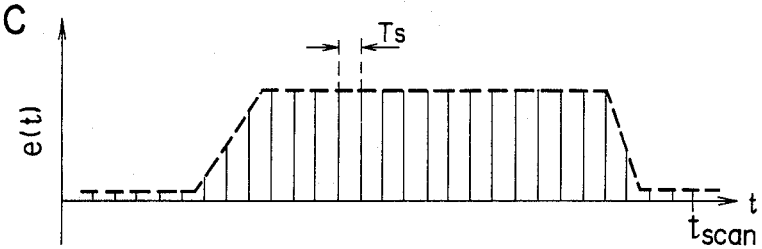
FIG. 24C
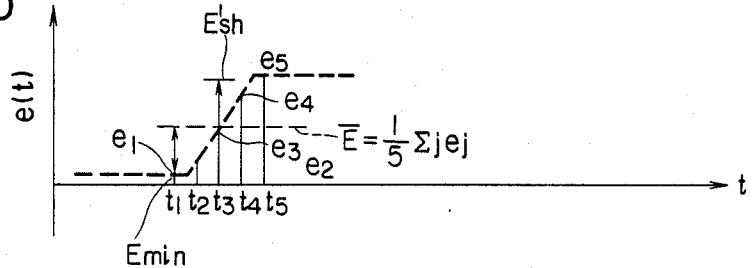
FIG. 24D FIG. 35
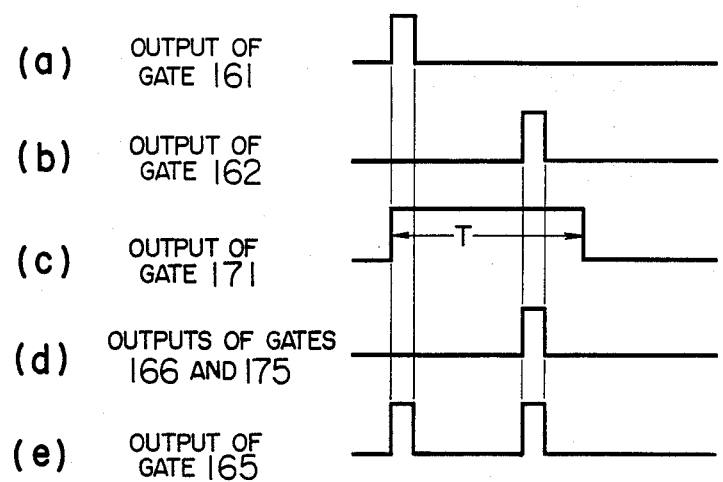
FIG. 36 FIG. 37
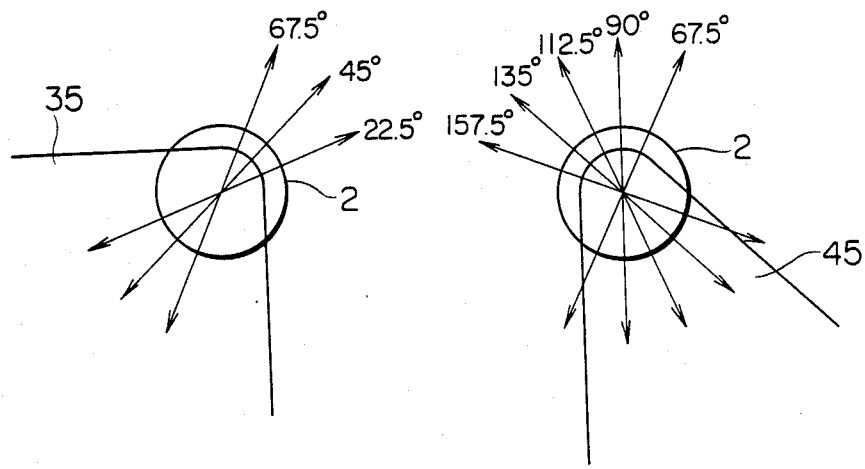
FIG. 38A FIG. 38B
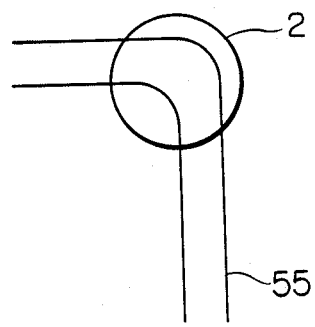 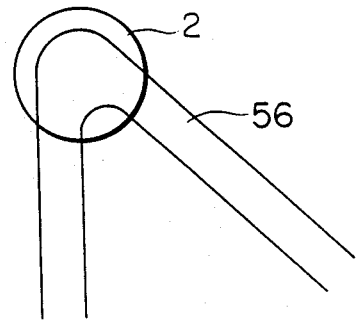

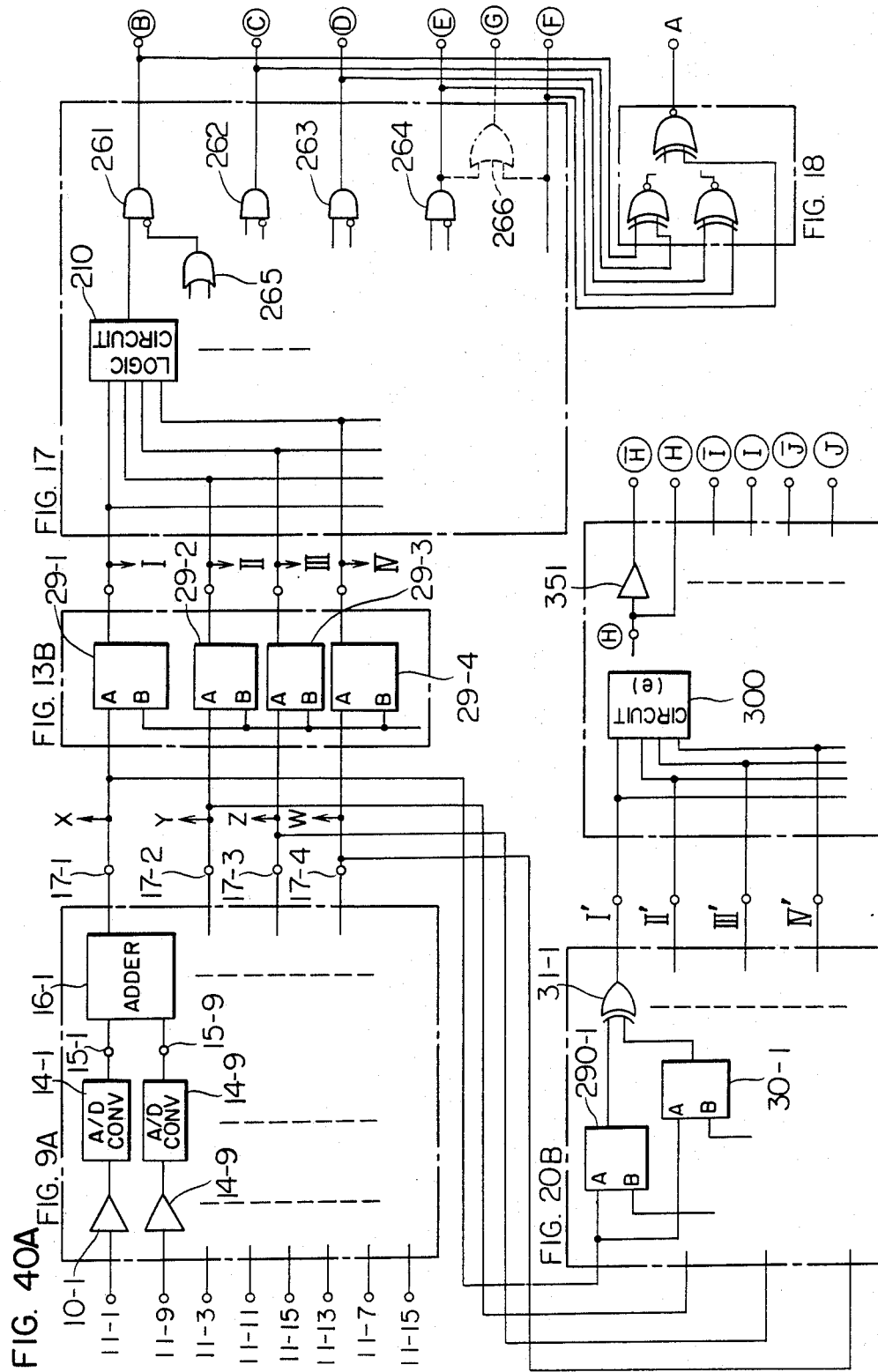

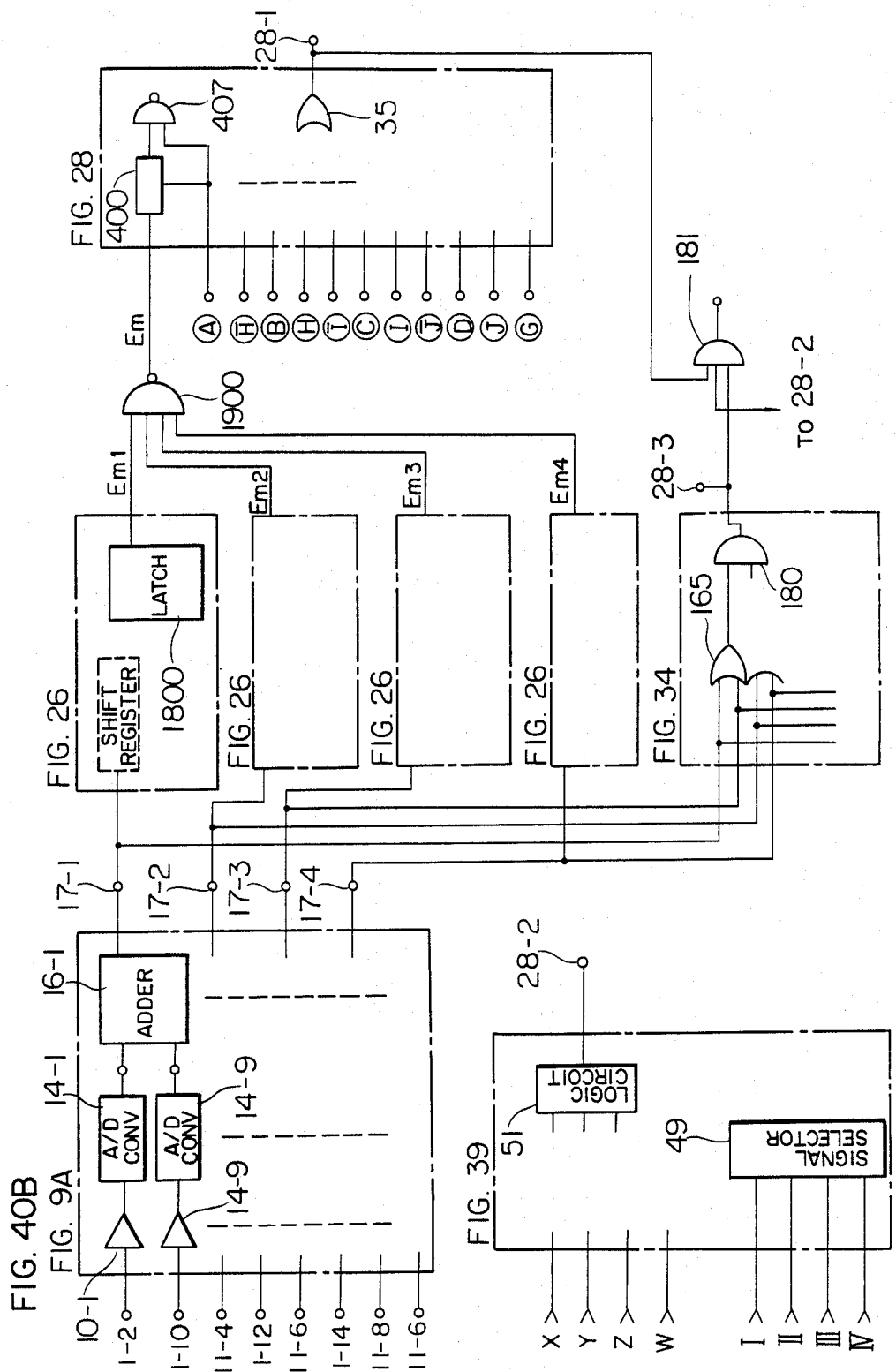

PATTERN DEFECT INSPECTION APPARATUS

BACKGROUND OF THE INVENTION

1. FIELD OF THE INVENTION

The present invention relates to a pattern defect inspection apparatus which optically and non-contactly inspects a pattern of an integrated circuit device or the like formed on a semiconductor wafer, and more particularly to a pattern defect inspection apparatus which detects a defect in a pattern by utilizing a reflected diffraction light from a pattern.

2. BACKGROUND OF THE INVENTION

It is essential to check whether any defect is included in or any foreign material is deposited on a pattern formed on a semiconductor wafer in order to improve the yield in the manufacture of a semiconductor device.

To this end, a personal visual inspection has been performed. However, as the pattern size of the device is microminiaturized, such a visual inspection has become more and more difficult to attain, and so an effective automatic inspection has been desired.

For such demands, various methods have been proposed, such as (1) measurement of a pattern size by utilizing a laser beam or an electron beam, (2) extraction of a defect by utilizing the laser beam or the electron beam, (3) detection of foreign material by a linearly polarized laser irradiation and an optical microscope (including a detector) having deflection plates, (4) detection of a defect by comparing two picture images obtained from two image pick-up devices, such as ITV cameras (industrial television cameras) which image a pattern under inspection by two object lenses of optical microscopes, and (5) extraction of a characteristic of a pattern by analyzing the number and the directions of diffraction lights by edges of a laser beam by a plurality of light detection cells arranged cylindrically.

However, those methods are not suitable to test a defect in a pattern formed on a wafer of the type to which the present invention is directed for the following reasons.

In general, the personal inspection method, such as inspection by use of a microscope is not significantly affected by the object to be inspected. The methods (1) and (2) belong to the inspection method using a microscope. On the other hand, the methods (4) and (5) are automated forms of the personal inspection methods.

Those methods have advantages and disadvantages. The methods (1) and (2) have a disadvantage in that the inspection time is long and hence they are not suitable for use to inspect a semiconductor device in the course of a production line without taking out the semiconductor device from the line; that is, they are not applicable to a process in-line test. They are frequently utilized for a sample which transmits light, such as a photo-mask. The method (3) may be applied to a wafer which does not transmit light but it can detect only foreign material and not defects. The method (4) may be applied to a wafer, but it detects a normal area as a defect unless patterns are identical because of comparison of identical patterns. The method (5) is suitable for a photomask, but not applicable to a wafer.

As approaches to resolve the above problems, pattern defect inspection apparatus have been proposed disclosed in the assignee of the present application such as by Japanese Utility Model Application Laid-Open Nos. 55-176555 and 57-22239 and Japanese Patent Application Laid-Open No. 58-206949.

In those proposed inspection apparatus, reflected diffraction lights created by scanning a surface of an integrated circuit pattern by use of a coherent light of a predetermined light spot diameter in a normal direction with respect to the surface of the pattern is detected by light detection means arranged in a plurality of spatial areas at which the reflected diffraction lights created by a normal integrated circuit pattern does not normally reach, so that a defect in the integrated circuit pattern is detected. Various defects generated in a patterned integrated circuit or a large scale integrated circuit pattern chip (or pellet), which hardly could be detected in the past, can be optically and non-contactly detected without comparison.

In the above apparatus, however, if the pattern formed on the wafer deviates from an ideal one, any error which causes no practical problem is detected as a defect. Further, when a circular pattern having a diameter which is larger than that of the light spot is tested, it may be determined defective in spite of the fact that the circular pattern per se is not a defective pattern.

Prior to the description of the embodiments of the present invention, a diffraction phenomenon which is caused when a light beam is irradiated onto a pattern formed on a wafer is explained with reference to FIGS. 1A–1E, 2A and 2B.

FIGS. 1A to 1E show projections, on the same plane as the wafer, of reflected diffraction lights (spread into a reflection space because the wafer does not transmit a visible-band light therethrough) which are generated when the light beam is irradiated onto a strip pattern formed on the wafer.

In FIG. 1A, a direction of the edges of the strip pattern 1-$a$ is incidental to a direction of an x-axis shown in FIG. 1E, and in FIGS. 1B, 1C and 1D, it makes an angle of 45°, 90° and 135°, respectively, with the x-axis. The directions of the reflected diffraction lights generated when the light beam 2 shown by a broken line circle is irradiated onto the strip patterns make an angle of 90° (right angle) to the respective pattern edges. In FIGS. 1A, 1B, 1C and 1D, 3-$a$, 3-$b$, 3-$c$ and 3-$d$ denote the directions of reflected diffraction lights, respectively. It is theoretically clear and experimentarily proven that the diffraction light produced by an edge is generated in the manner shown in FIG. 1.

The pattern formed on the wafer includes straight edges except for a circular pattern and an arcuate pattern and the directions thereof are limited to 45°, 90° and 135° relative to the direction of a reference pattern edge (referred to as the x-axis). FIGS. 1A to 1D show those four directions. FIG. 1E shows the directions of the reflected diffraction lights generated orthogonally to those four directions, shown in superposition. The characteristics of the reflected diffraction lights summarized in FIG. 1E are as follows. (1) The reflected diffraction lights from a normal pattern formed on the wafer regularly distribute and have predetermined directions, that is, 0°, 45°, 90° and 135°. Those directions are hereinafter referred to as normal directions and are designated by I, II, III and IV, respectively. (2) There are spatial areas which the reflected diffraction lights from the normal pattern do not normally reach or at which the light is very weak. Those areas are designated by A–D and A'–D'. They have four central directions, that is, 22.5°, 67.5°, 112.5° and 157.5°. Those are referred to as abnormal directions. (3) The intensity of the reflected diffraction light by the edge is proportional to the length of the edge irradiated by the light beam.

FIGS. 2A and 2B illustrate a defect in the pattern. In FIG. 2A, numeral 1 denotes a portion of the pattern and numeral 2 denotes a light beam having a circular cross-section.

Edges are designated by ①, ②, ③ and ④. The edges ①, ② and ③ are normal and the edge ④ is a defective edge having a portion thereof cut away.

The light beam is reflected and diffracted normally to the edges so that the diffraction light patterns appear as shown in FIG. 2B, in which ①, ② and ③ denote the diffraction light patterns by the normal edges and ④ denotes the diffraction light pattern in the abnormal direction by the defective edge. Since the edge 3 is shorter than other edges, the intensity of the diffraction light is lower. This is shown in FIG. 2B by the shorter pattern ③.

As described above, the intensity of the reflected diffraction light by the edge is proportional to the length of the edge irradiated by the beam. For this reason, the reflected diffraction light by the edge ③ in FIG. 2A is shown relatively short as shown by ③ in FIG. 2B.

It is thus seen that in order to detect a pattern defect on the wafer, lights in abnormal directions reaching the eight areas A, B, C, D, A′, B′, C′ and D′ should be detected.

Where photo-detectors are arranged in the spatial areas A-D and A′-D′, the reflected diffraction lights in the normal directions I-IV by the normal patterns are not detected by the photo-detectors but the reflected diffraction lights in the abnormal direction by the defective pattern or the foreign material are detected by the photo-detectors. This is a principle of detection of a defect.

Referring to FIGS. 3A, 3B and 4, a defect test apparatus in accordance with the above principle, which was proposed by the assignee of the present application (see Japanese Utility Model Application Laid-Open No. 57-22239) is explained, and problems associated therewith are discussed with reference to FIGS. 5A to 5F.

FIGS. 3A and 3B show spatial arrangements of detectors for detecting defects. The direction along which the areas A-A′ shown in FIG. 1E extend is represented by x′. FIG. 3A shows the arrangement of the detectors in a first quadrant on a z-x′ plane and FIG. 3B shows the arrangement of the detectors projected on an x-y plane (wafer surface). In FIG. 3A, numeral 4 denotes a light beam which scans a wafer 5, numerals 6-1 and 7-1 denote lenses for condensing reflected diffraction lights, numerals 6-2 and 7-2 denote lenses for directing the condensed lights to detectors 9-1 and 9-2, numerals 8-1 and 8-2 denote stray light blocking slits, numerals 9-1 and 9-2 denote the photo-detectors and numerals 10-1 and 10-2 denote pre-amplifiers. One detection system comprises 6-1, 6-2, 8-1, 9-1 and 10-1. Numeral 11 denotes a component of the reflected diffraction light from the defect (including foreign material), which is directed to the detector. This is hereinafter referred to as a signal light. Sixteen such detection systems each comprising 6-1 to 10-1, for example, are arranged as shown in FIG. 3B.

FIG. 3B shows an overall arrangement of the above-mentioned detection systems projected on the x-y plane (wafer surface). Photo-detectors 9-1 to 9-16 are shown to represent the detection systems.

As shown in FIGS. 3A and 3B, $\theta$ represents an angle between a z-axis and an axis of the detection system, and $\phi$ represents an angle between an x-axis and the axis of the detection system projected on the x-y plane. In order to detect the defects on the wafer, the detection systems each having at least one detector (two detectors in the arrangements shown in FIGS. 3A and 3B) are arranged in the eight abnormal direction areas. The construction of the detection systems is disclosed in detail in the above-referenced application (Utility Model Application Laid-Open No. 57-22239).

The outline of the inspection method of a wafer on which is formed patterns utilizing the above-mentioned detection system is as follows.

The wafer is mounted on a wafer table which is attached to an X-Y stage. A laser beam is scanned to inspect the wafer surface. The entire surface of the wafer is inspected by two-dimensionally scanning the laser beam or one-dimensionally scanning the laser beam while one-dimensionally moving the stage.

FIG. 4 is a block diagram for processing detection signals thus derived. Numeral 11 denotes the signal light, numeral 12-1 denotes a detection unit including a plurality of detection systems, numeral 13-1 denotes an analog amplifier unit including a plurality of analog amplifiers one for each of the detection systems, numeral 14 denotes a signal converter which converts as many signals as the number of detection systems into a single signal by analog-summing one half of the signals in positive polarity and the other half of the signals in negative polarity to eliminate D.C. components contained in the signals, numeral 15 denotes a full-wave rectifier, numeral 16 denotes an envelope detector, numeral 17 denotes a comparator and numeral 18 denotes a binary signal output terminal.

The defect inspection apparatus comprising the detection systems and the signal processing systems as described above has no problem in the ability of detecting a defect. However, it has the following practical problems. The characteristics (1) and (2) of the reflected diffraction lights described above are valid for an ideal pattern formed on the wafer. The ideal pattern is a pattern exactly formed as instructed by a design drawing. A lithography technique is used to form the pattern on the wafer. Because of a limitation by the lighography technique, the resulting pattern deviates from the ideal pattern. There are two deviations which are likely in the inspection of the pattern defects. One is roundness at a corner and the other is fine disturbance in the edge (hereinafter referred to as edge disturbance). Because of those two deviations, the characteristics (1) and (2) described above are not valid.

Referring to FIGS. 5A to 5F, problems encountered in detecting a defect in the actual wafer are discussed. FIGS. 5A to 5F show reflected diffraction lights for two patterns having round corners and one strip pattern having an edge disturbance. In FIG. 5A, the junction area of pattern edges ① and ② is round, in FIG. 5C, a junction area of the edges ① and ② is round, and in FIG. 5E, one side of the stripe has the edge disturbance. In FIG. 5A, when the corner area is irradiated by a light beam shown by a broken line circle 2, the reflected diffraction lights produced by the edges ① and ② are shown by ① and ② in FIG. 5B. If it is an ideal pattern, the directions of the reflected diffraction lights are limited to those two. However, weak lights ⓐ, (i) and (ii) are generated at the round corner area. The light ⓐ is in the normal direction (45°) and does not raise a problem in detecting the defect but the lights (i) and (ii) are in the abnormal directions (22.5° and 67.5°) and they are detected by the detection systems arranged in those directions so that the round corner is determined to be a defect. The above description is also applicable to the patterns shown in FIGS. 5C and 5E, and the round corner and the edge disturbance are determined as the defects.

Next, the case of the corner shown in FIG. 5C will be explained. If it is an ideal pattern, the reflected diffraction lights will be only in the normal directions ① and ② shown in FIG. 5D. However, because of the round corner, weak lights ⓐ and ⓑ in the normal directions and weak lights (i) to (iii) in the abnormal directions are generated and the lights in the abnormal directions are detected so that a defect is indicated.

In the strip pattern of FIG. 5E, if it is an ideal pattern having no edge disturbance, the reflected diffraction lights will be only in the normal directions ① and ①' as shown in FIG. 5F. However, because the edge disturbance, light ⓐ in the normal direction and lights (i) and (ii) in the abnormal direction are generated and the lights in the abnormal directions are detected so that a defect is indicated. The condition of FIG. 5F varies in different ways depending on the edge disturbance.

The above deviations from the ideal pattern are inherent to the process and they are not defects from the standpoint of the device function. If such deviations from the ideal pattern are detected, even a pattern which causes no practical problem is determined as a defective pattern.

To summarize the prior art problems, the prior art wafer inspection apparatus can inspect the wafer having a light-nontransmissible pattern formed thereon and has a sufficient detection ability, but since the pattern formed on the wafer deviates from the ideal pattern, the apparatus identify the deviated areas as defects.

SUMMARY OF THE INVENTION

It is an object of the present invention to provide a pattern defect inspection apparatus which can extract only those defects on a pattern formed on a semiconductor wafer which are to be detected as defects without detecting minor deviations from an ideal pattern which do not lead to a fatal problem.

It is another object of the present invention to provide a pattern defect inspection apparatus which detects a defect in a pattern formed on a semiconductor wafer and a foreign material deposited on the wafer by utilizing reflected diffraction lights and which has a function to determine a pattern which includes an abnormality, but does not cause a practical problem as a non-defective pattern.

It is other object of the present invention to provide a pattern defect inspection apparatus which does not identify a circular pattern formed on a semiconductor wafer as a defect.

In order to achieve the above objects, in accordance with one aspect of the present invention, the pattern defect inspection apparatus detects the reflected diffraction lights from the normal pattern, that is, the normal direction signals, classifies the normal patterns and determines the normality/abnormality at different levels for the respective normal patterns when the reflected diffraction lights from the abnormal pattern, that is, the abnormal direction signals are applied so that it determines whether the abnormal direction signals represent a true defect or a practically acceptable defect.

BRIEF DESCRIPTION OF THE DRAWINGS

FIG. 10 is a diagram which shows relations between direction symbols and normal directions;

FIGS. 11 and 12 are diagrams used to explain the present invention;

FIGS. 13A and 13B show circuits for generating the normal direction signals;

FIG. 14 shows a circuit for generating a classifying signal for a major class 1;

FIG. 19 is a diagram which illustrates a sub-class pattern;

FIG. 23 is a diagram which shows a signal waveform by the reflected diffraction light;

FIGS. 24A to 24D are diagrams used to explain a principle of a floating threshold type detection circuit;

FIG. 35 is a diagram which illustrates the operation of the circuit of FIG. 34;

FIGS. 36, 37, 38A and 38B are diagrams used to explain another normal/abnormal discriminator shown in FIG. 39;

FIGS. 40A and 40B collectively show an overall circuit arrangement of a signal processing circuit of the pattern defect inspection apparatus of the present invention.

DESCRIPTION OF THE PREFERRED EMBODIMENTS

The detection principle in accordance with the present invention is outlined below.

(1) The reflected diffraction lights, not only in the abnormal directions but also in the normal directions are simultaneously detected.

(2) The normal direction signals are generated by the normal patterns and include information such as directions of edges of the patterns and the number of directions of the edges. The pattern on the wafer is classified by utilizing the information.

There are two methods in detecting the abnormality in the pattern by using the detected normal direction and abnormal direction signals. In a first method:

(3) The detected abnormal direction signals are discriminated by normal/abnormal discriminators provided one for each of a plurality of classes of patterns.

Since the normal/abnormal discrimination criterion can be established for each pattern, the defect can be precisely and reliably determined.

In a second method:

(4) All of the abnormal direction signals are summed, the sum is compared with a predetermined threshold and if the sum is larger, a defect in the pattern is determined.

(5) If the sum is smaller than the threshold, a signal which is in a predetermined magnitude order is selected from the signals generated by the reflected diffraction lights in the normal directions generated by the pattern, a signal which is in a predetermined magnitude order is selected from the signals generated by the reflected diffraction lights in the abnormal directions, and the defect in the pattern is determined depending on which one of the signals is larger (or smaller) than the other.

In addition, it is possible to add to the pattern defect inspection apparatus according to the first and/or second method a circuitry by which a circular pattern having a large diameter relative to a light beam diameter is not determined as a defect.

Figure 6:
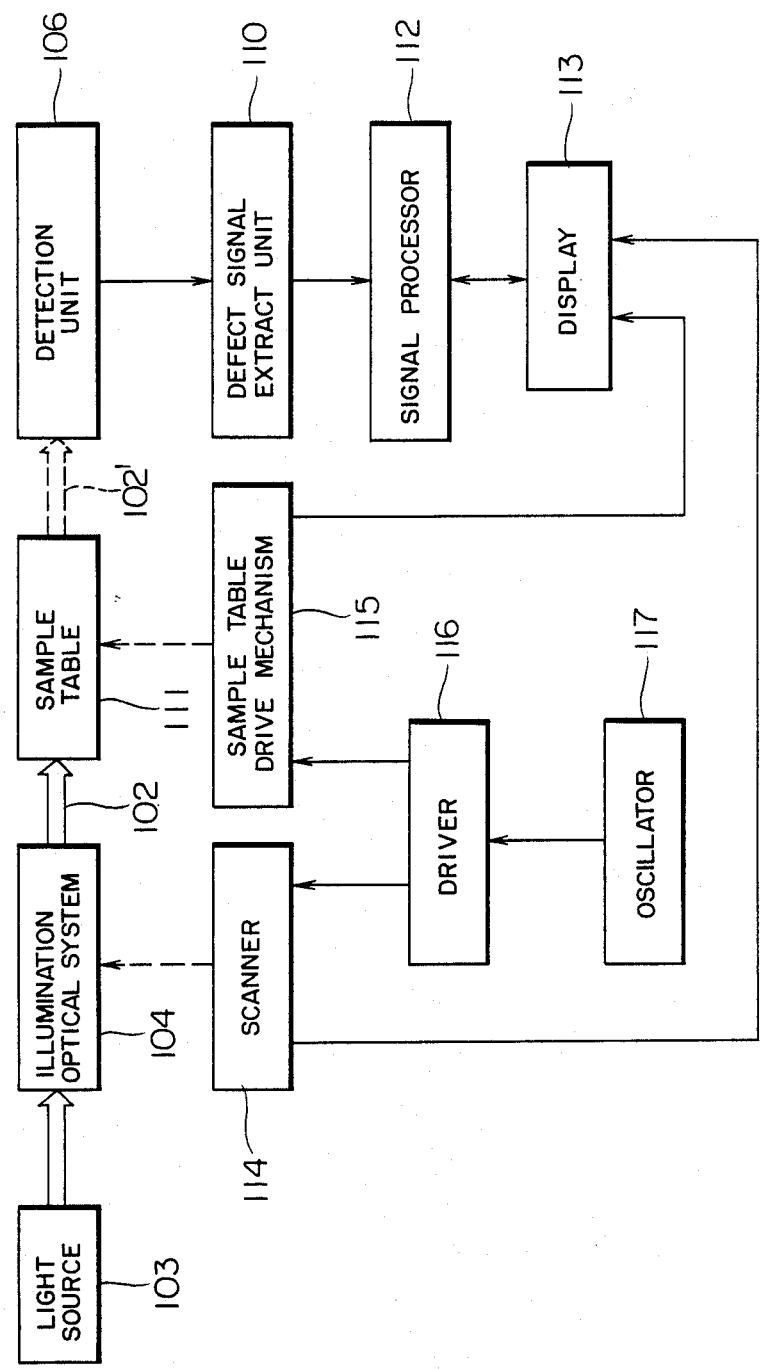
FIG. 6 is a block diagram which shows a pattern defect inspection apparatus of the present invention.

FIG. 6 is a block diagram of an overall configuration of a pattern defect inspection apparatus of the present invention.

The present apparatus comprises a light source 103, an illumination optical system 104, a sample table (or a table on which is mounted an object to be inspected) 111 on which a sample (chip having an integrated circuit patterned thereon) is mounted, a detection unit 106, a defect signal extraction unit 110, a signal processor 112, a display 113, a light beam or laser beam scanner 114, a sample table drive mechanism 115, a driver 116 for the scanner 114 and the sample table drive mechanism 115, and an oscillator 117 which is an input signal source to the driver 116.

Defect signals extracted by the defect signal extraction unit 110 are sent to the signal processor 112 where they are summed and the resulting sum signal is converted to a signal compatible to an output device such as a display or a recorder for the inspection result. For example, when a two-dimensional display is to be effected in synchronism with the scan of the light beam 102 on the integrated circuit chip, a luminance modulation signal compatible to a characteristic of the display 113 is produced.

The two-dimensional scan of the light beam 102 on the chip may be effected by deflecting the light beam along an x-axis and moving the sample table 111 along a y-axis. The light beam 102 may be defected by a galvano mirror, a rotating mirror or other similar means. The deflection means is included in the illumination optical system 104. The scanner 104 supplies a motive force to the deflection means.

The drive 116 drives the scanner 114 and the sample table drive mechanism 115, and the oscillator 117 comprises an oscillator which produces an output at a frequency which determines the velocity of the scanner 114 and a frequency divider which frequency-divides the output of the oscillator to a frequency which determines a velocity of the sample table 111. Two synchronization signals to the display 113 are generated by the driver 116 and the sample table drive mechanism 115.

In FIG. 6, the diffraction light by the defect is designated by 102' to discriminate it from the light beam 102 incident to the sample surface.

In the apparatus of FIG. 6, the units other than the detection unit 106 and the defect signal extraction unit 110 are similar to those shown in the prior application, and the units 106 and 110 are characteristic portions of the present invention.

Figure 7:
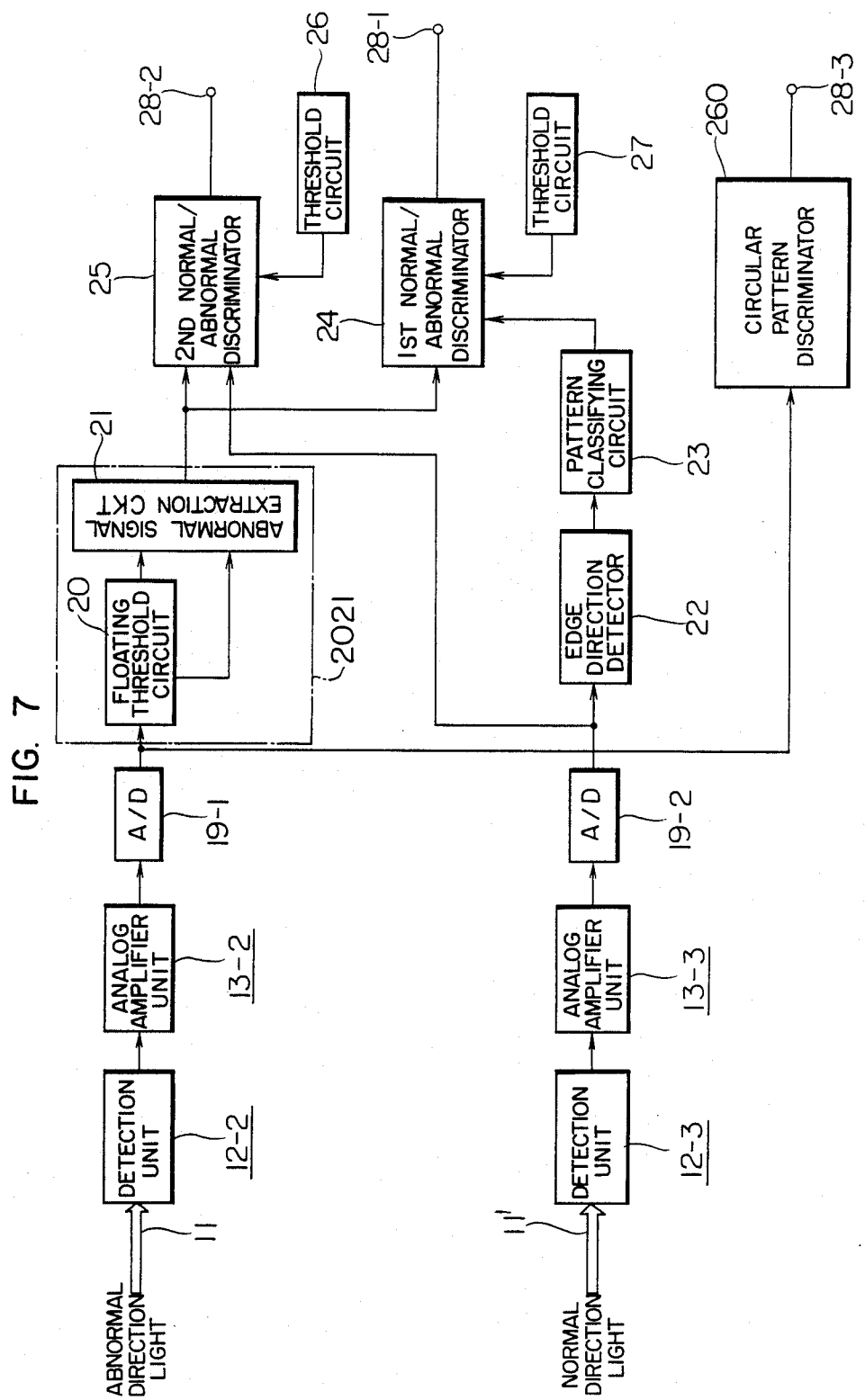
FIG. 7 is a block diagram of a signal processing circuit of the present invention.

FIG. 7 is a block diagram of an embodiment of the signal processor in the present invention. It shows a detail of the detection unit 106 and the defect signal extraction unit 110. Numeral 11 denotes a signal light in the normal direction, numerals 12-2 and 12-3 denote detection units each comprising a plurality of detection systems, numerals 13-2 and 13-3 denote analog amplifier units each comprising a plurality of analog amplifiers one for each of the detection systems, numerals 19-1 and 19-2 denote A/D converters, numeral 20 denotes a floating threshold type detection circuit, numeral 21 denotes an abnormal signal extraction circuit, numeral 22 denotes an edge direction detector, numeral 23 denotes a pattern classifying circuit, numeral 24 denotes a normal/abnormal discriminator for discriminating if the extracted abnormal signal is for a true defect or not in accordance with the first method described above, numeral 25 denotes a normal/abnormal discriminator which compares the magnitudes of the extracted abnormal signal and the normal direction signal in accordance with the second method described above, numeral 260 denotes a circular pattern discriminator which does not determine a circular pattern as a defect, numerals 26 and 27 denote digital threshold circuits, and numerals 28-1, 28-2 and 28-3 denote terminals from which true defect signals determined by the normal/abnormal discriminators are outputted. The floating threshold type detection circuit 20 and abnormal signal extraction circuit 21 constitute an abnormal direction signal detection circuit 2021. It is to be noted that although the first and second normal/abnormal discriminators are shown in one and the same figure i.e. FIG. 7, for the sake of convenience, they may be independently used to produce defect signals or, as explained later, the outputs 28-1 and/or 28-2 of the first and second discriminators may be used in combination with the output 28-3 of the circular pattern discriminator to produce a defect signal.

Figure 4:
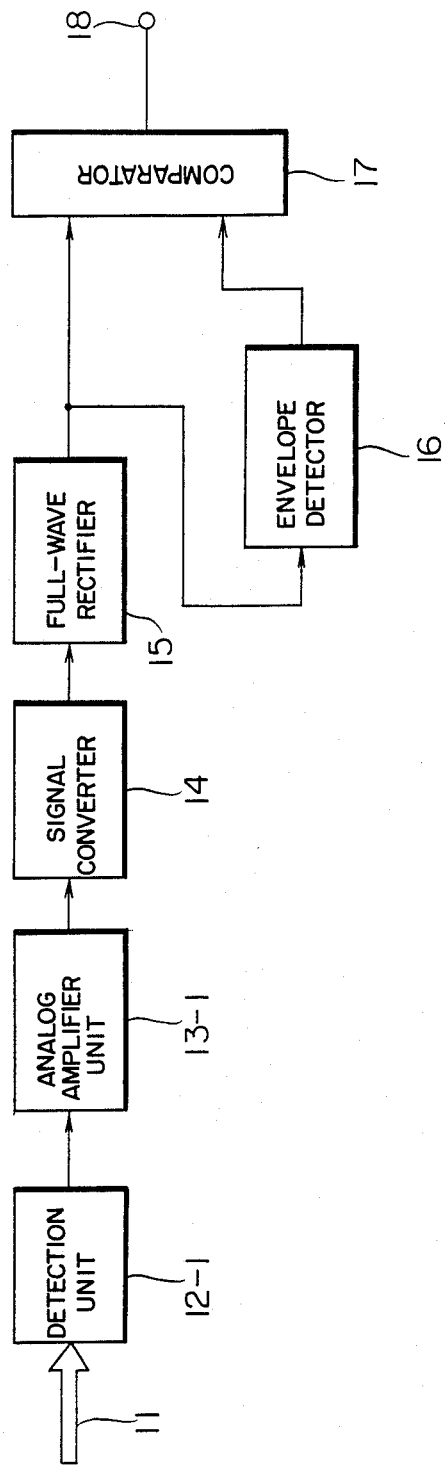
FIG. 4 is a block diagram of a processing circuit for detection signals from the defect detectors of FIGS. 3A and 3B.
Figure 5A:
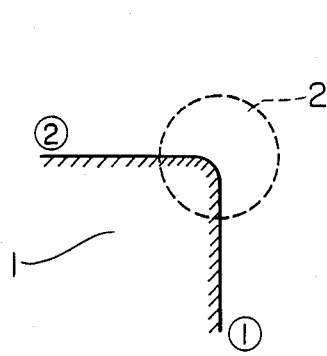
FIGS. 5A to 5F are diagrams used to explain the present invention.
Figure 5B:
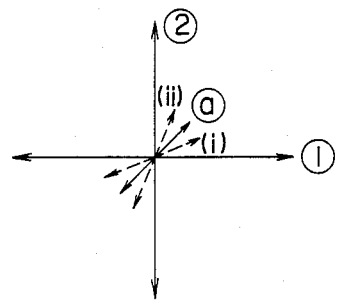
Figure 5C:
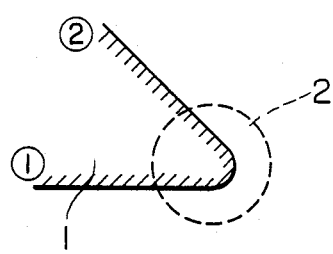
Figure 5D:
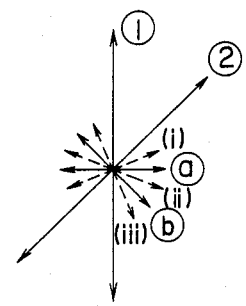
Figure 5E:
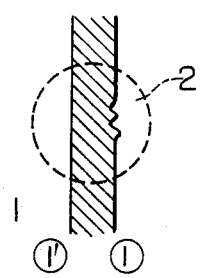
Figure 5F:
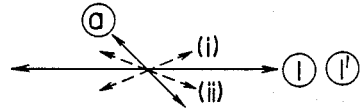

The differences between the embodiment of FIG. 7 and the configuration of FIG. 4 are as follows.

(1) Detection system: In the prior art configuration, only the signal lights in the abnormal directions are detected. In the present embodiment, the signal lights in the normal directions are detected as well.

(2) Extraction of abnormal signal: In the prior art configuration, an analog threshold is used to extract the abnormal signal in a binary form. In the present embodiment, the signal is a multi-digit signal (e.g. 8-bit digital signal) and is compared with a digital threshold to extract the abnormal signal. Accordingly, the extracted abnormal signal may be either binary or multi-level.

In the present embodiment, the signal lights in the normal directions are detected to discriminate the normal/abnormal extracted signals.

As seen from the above, the prior art configuration and the present embodiment are different in basic concept from each other. The elements of the present embodiment are now explained in sequence.

Figure 8A:
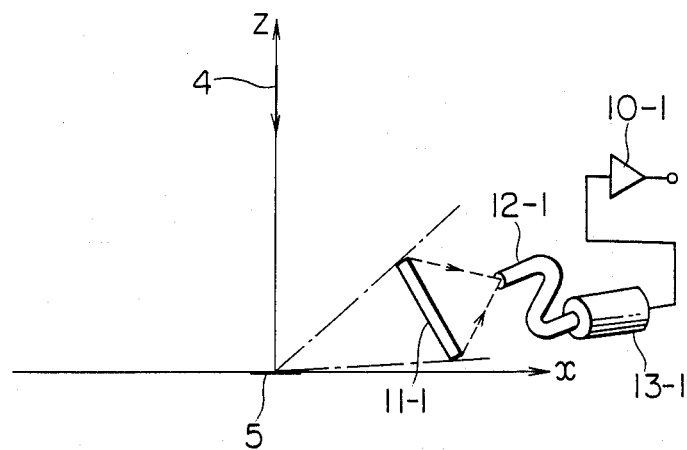
FIGS. 8A and 8B are diagrams which show arrangement of defect detectors in the present invention.
Figure 8B:
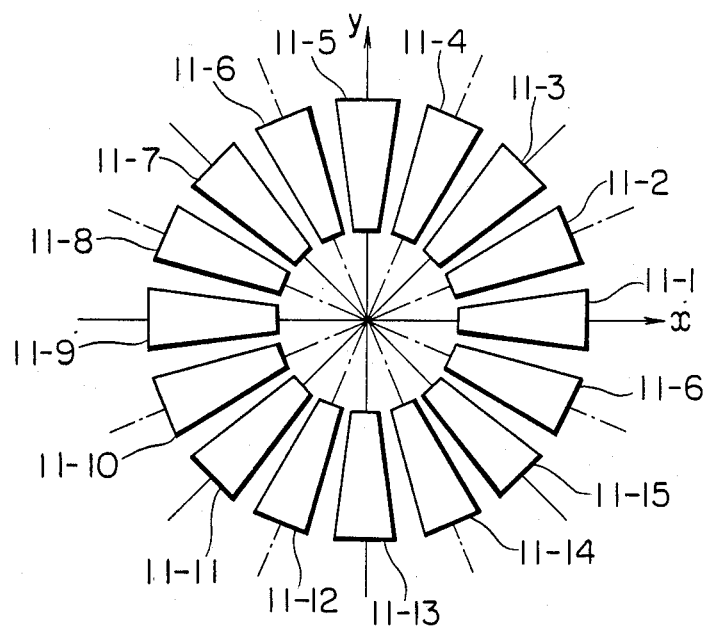

FIGS. 8A and 8B show the detection units 12-2 and 12-3. FIG. 8A shows the arrangement of the detection systems in a first quadrant on a z-x plane, and FIG. 8B shows the arrangement of the detection systems projected on an x-y plane. Numerals 11-1, . . . 11-16 denote condensers having wide light receiving areas (for example, stripe-shaped Fresnel lenses), numerals 12-1, . . . 12-16 denote light transmission elements such as optical fibers (only 12-1 is shown), numerals 13-1, . . . 13-16 denote photo-detectors (only 13-1 is shown), and numerals 10-1, . . . 10-16 denote pre-amplifiers paired with the respective photo-detectors (only 10-1 is shown). As seen from the comparison with the defined directions I, II, III and IV, the detection systems having odd-number subscripts such as 11-1, 12-1, 13-1 and 10-1 constitute the normal direction detection unit 12-3, and the detection systems having even-number subscripts such as 11-2, 12-2, 13-2 and 10-2 constitute the abnormal direction detection unit 12-2. Sixteen such detection systems, eight in the abnormal directions ($\phi=22.5°$, 67.5°, 112.5° and 157.5°) and eight in the normal directions ($\phi=0°$, 45°, 90° and 135°) are arranged as shown in FIG. 8B.

Figure 3A:
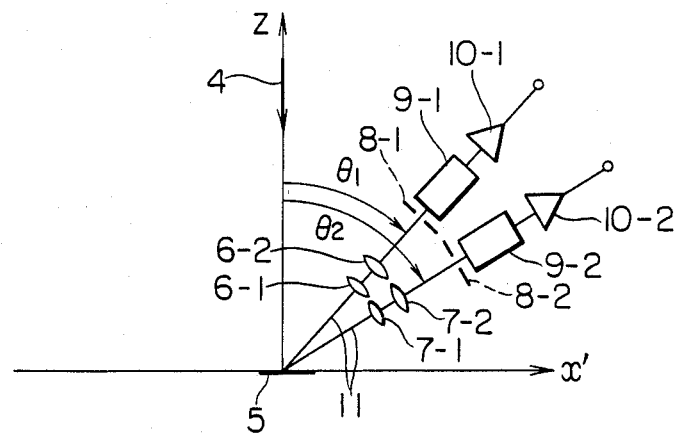
FIGS. 3A and 3B are diagrams which show the spatial arrangement of defect detectors.
Figure 3B:
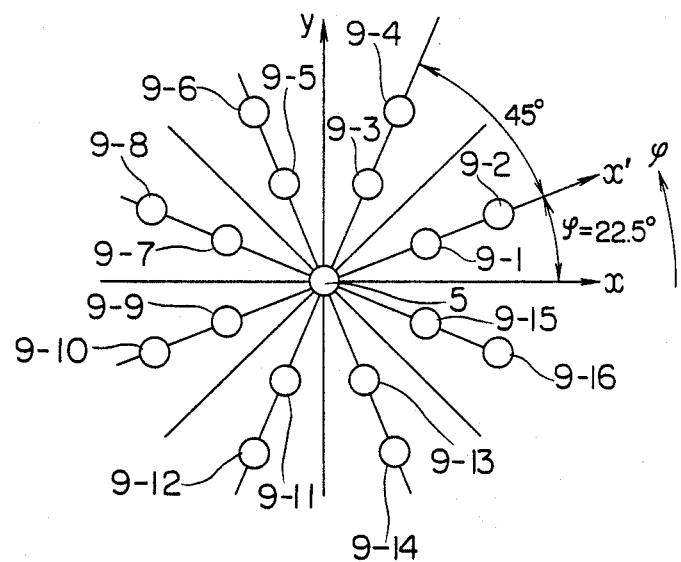

Differences from the prior art configuration shown in FIGS. 3A and 3B are that the signal lights in the normal directions are detected, and one condenser lens having a wide area is arranged in each direction. By use of the wide area condenser, (1) misdetection of a defect of a specific size is reduced, and (2) a signal having one-to-one correspondence to the defect size is produced. The advantage (1) is further explained. When the pattern size under inspection and the intensity of the reflected diffraction light from the pattern are plotted in a graph with the pattern size on an abscissa and the intensity on an ordinate, it is seen that the intensity periodically varies with the increase of the pattern size. The intensities of the reflected diffraction lights from the patterns of specific sizes are low. And also, the intensity of the reflected diffraction light plotted with the various angles $\theta$ relative to the z-axis of the detection system shown in FIG. 3A exhibits a periodicity.

In order to increase the light receiving area of the condenser lens, the following methods may be used in addition to the above method: (a) As many square photoelectron multiplier tubes as are required are arranged; (b) as many one-dimension or two-dimension detector arrays as are required are arranged; (c) array detectors specifically designed for the present apparatus are arranged. When they are used, the light transmission element 12-1 is not necessary. The light transmission element need not be usually used if there is an enough space to realize the apparatus.

In this manner, eight detection signals are produced in the normal directions and eight detection signals are produced in the abnormal directions. For the purpose of the following description, the handling of those signals is explained with reference to FIGS. 9A and 9B.

The eight normal directions and the eight abnormal directions are grouped respectively and direction signals representing four directions are produced in each group.

In the present invention, the detected signals by the reflected diffraction lights are processed in digital form. In order to digitize the signals, the eight signals are digitized and the digital signals obtained from the condensors placed in the opposite directions with respect to the origin of x-y coordinate shown in FIG. 8B are summed (first summation method), or the analog signals in the eight directions are summed and the sum is digitized (second summation method).

Figure 9A:
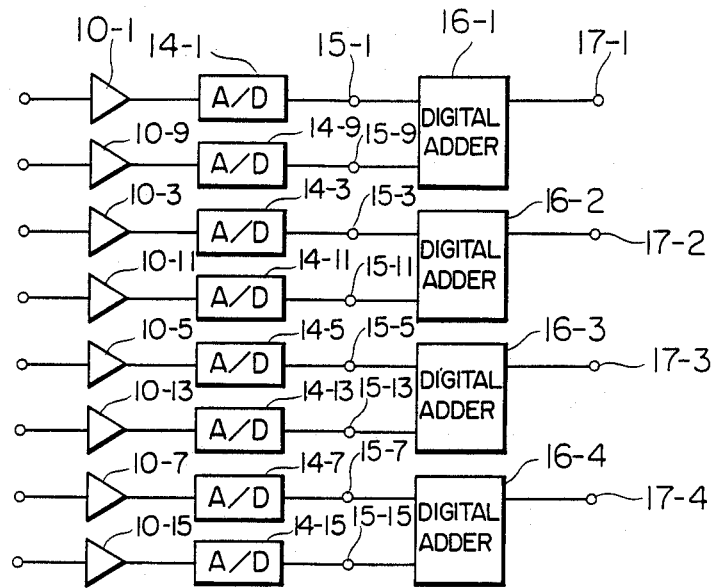
FIGS. 9A and 9B show circuits which convert analog signals by the reflected diffraction lights to digital signals.

FIG. 9A shows the analog amplifier units 13-2 and 13-3 and the D-A converters 19-1 and 19-2 under the first summation method. Numerals 10-1, 10-3, . . . , 10-15 (having odd-number subscripts) denote the pre-amplifiers, numerals 16-1, 16-3, . . . , 16-15 denote digital adders, numerals 14-1, 14-3, . . . , 14-15 denote A/D converters, numerals 15-1, 15-3, . . . , 15-15 denote output terminals of the A/D converters, and numerals 17-1, 17-2, 17-3 and 17-4 denote output terminals for signal channels in the normal directions. The signal channels for the abnormal directions are designated by the numerals having even-number subscripts.

In operation, the output signals from the eight pre-amplifiers 10-1, 10-3, . . . , 10-15 (having odd-number subscripts) are digitized by the A/D converters 14-1, 14-3, . . . 14-15. The paired digital signals, for example, 15-1 and 15-9, are summed by the adders 16-1, 16-2, 16-3 and 16-4. In this manner, four digital signals 17-1 to 17-4 for the normal directions are produced.

By replacing the elements shown in FIG. 9A with the elements designated by even-number subscripts, four digital signals for the abnormal directions are produced.

Figure 9B:
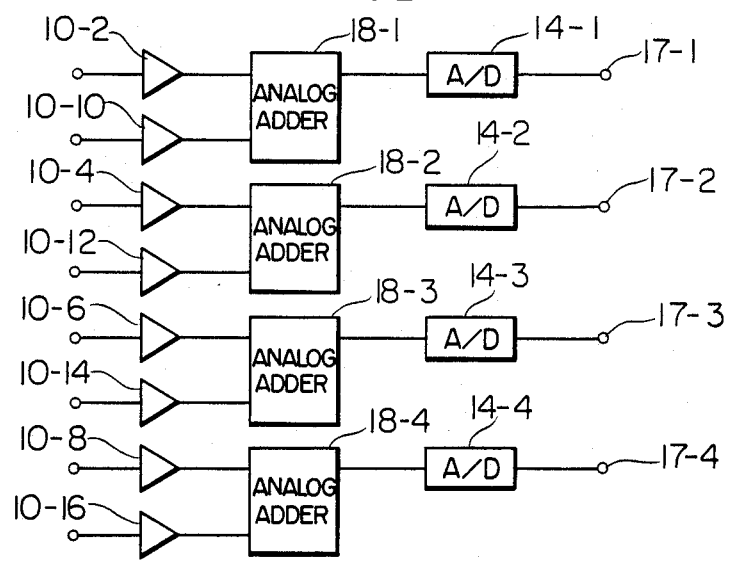

FIG. 9B shows a configuration when the second summation method is applied to the abnormal direction signals. Paired analog signals in the respective directions, for example, 10-2 and 10-10 are summed by an adder 18-1 and the sum output thereof is digitized by an A/D converter 14-1. Other paired signals in other directions are similarly processed so that four digital signals 17-1 to 17-4 for the abnormal directions are produced.

By replacing the elements shown in FIG. 9B with elements designated by odd-number subscripts, four digital signals for the normal directions may be produced.

The four normal direction signals are designated by I, II, III and IV shown in FIG. 10. Under this convention, when the configurations of FIGS. 9A and 9B are for the normal directions, the direction signals at the output terminals 17-1, 17-2, 17-3 and 17-4 are I, II, III and IV, respectively.

As described above, there are mainly two methods, first and second methods for determining the defect in the pattern. The first determination or discrimination method is first explained.

First Determination Method

The first determination or discrimination method comprises three major steps. Step A: The pattern on the wafer is classified (i.e. major classification) based on the normal direction signals while utilizing the pattern edge direction signals. Step B: The pattern is sub-classified (i.e. sub-classification) based on the normal direction signals while utilizing the round corner direction signals. Step C: Normal/abnormal discriminators are provided one for each of as many patterns as are determined by the number of two types of classification signals so that only a true defect signal is extracted from the abnormal signals.

In order to attain the major classification of the step A, it is necessary to produce the pattern edge direction signals. As explained before, a level of a signal generated perpendicularly to the edge is high. Accordingly, it is necessary to selectively produce only the high level signals in the directions I, II, III and IV. The formation of those signals will be described later.

Referring to FIGS. 11 and 12, the classification of the pattern is explained.

The characteristics of the pattern formed on the wafer have been already described with reference to FIGS. 1A-1D. It has been found that one of sixteen types of patterns as shown in the right column "Basic Circuit Pattern Type" in FIG. 11 can be selected when the pattern elements are extracted in accordance with geographical patterns. A normal pattern comprises one or more of those sixteen basic patterns.

The sixteen basic patterns are analyzed in accordance with the properties of the patterns, that is, the direction of the reflected diffraction light by the edge is normal to the edge, and the intensity in that direction is proportional to the length of the edge being irradiated.

Let us assume that the basic patterns shown in FIG. 11 are irradiated by light beams shown by broken line circles. Only high intensity lights are considered. The directions of the reflected diffraction lights from the basic patterns are shown in FIG. 11 by the diffraction directions I, II, III and IV. The normal direction signals are generated in five cases, i.e. the number of the normal direction signals is 0, 1, 2, 3, and 4, which correspond to the classes of the basic circuit patterns.

Let us assume that the normal direction signals are generated in two directions simultaneously. The two directions may be orthogonal or oblique to each other. Those can be classified. When the normal direction signals are generated in three or four directions simultaneously, it corresponds to a composite pattern of the basic patterns, as seen from FIG. 11. For example, an upper pattern in a major class 5 of FIG. 12 is a composite pattern of a 135° oblique-crossing basic pattern in a major class 4 of FIG. 11 and a right angle basic pattern in a major class 3 of FIG. 11.

The above classes of patterns are referred to as major classes. As seen from FIG. 11, there are five major classes.

While the above analysis enables the major classification, it is insufficient to construct classifying circuits. In order to construct them, the orientations of the basic patterns on the wafer should be considered. For example, the edges of the basic patterns can be oriented in eight directions but four of them are sufficient for this purpose. FIG. 12 shows all directions of the reflected diffraction lights which vary with the orientation of each basic pattern.

FIG. 12 is briefly explained. Let us assume a 45° oblique crossing pattern. There are eight possible orientations of the pattern on the wafer and four basic directions. Two normal direction signals in the oblique directions to each other are generated for each of the four directions. The directions of the normal direction signals vary with the orientation of the pattern. The "number of cases" in FIG. 12 corresponds to the number of orientations of the pattern.

In this manner, the basic patterns are major-classified in accordance with the orientations of the pattern on the wafer.

The patterns may be sub-classified by subdividing each of the major classes 2 to 4 of FIGS. 11 and 12. For the convenience of explanation, the subclasses will be explained after the explanation of the major-classifying circuit.

Prior to the explanation of the major-classifying circuit, the generation of the direction signals is explained with reference to FIGS. 13A and 13B.

There are two methods of generating the direction signals. In FIG. 13A, the eight signals at the signal terminals 15-1 to 15-8 in FIG. 9A are used, and in FIG. 13B, four outputs 17-1 to 17-4 in FIG. 9A or 9B are used.

The basic patterns are classified based on high level direction signals. FIG. 12 shows the classifying circuit, the output signal of which may be binary (for example, High and Low). The digital input signal (corresponding to the high level direction signal) is compared with a digital threshold and if the former is larger it is determined as the high level signal. To this end, a digital comparator is appropriate. The circuits shown in FIGS. 13A and 13B use such digital comparators. In FIG. 13A, terminals 15-1, 15-9, 15-3, 15-11, 15-5, 15-13, 15-7 and 15-15 are connected to the terminals of the corresponding numerals in FIG. 9A to which the normal direction digital detection signals are applied, and those terminals are also connected to terminals A of the corresponding digital comparators 27-1, 27-2, ..., 27-8. A threshold voltage $V_{TH}$ of a predetermined level (H level) is supplied in common to terminals B of the digital comparators. The comparators 27-1 and 27-2 compare the digital input signals from the oppositely arranged condensors 11-1 and 11-9 (FIG. 13B) with the threshold voltage $V_{TH}$ at the terminal 8, and if both signals are larger than the level H, an AND gate 28-1 produces an H-level output so that the normal direction signal I is produced. Numerals 28-2, 28-3 and 28-4 denote AND gates which produce normal direction signals II, III and IV, respectively. In the circuit shown in FIG. 13B, input terminals 17-1 to 17-4 are connected to the corresponding terminals in FIG. 9A so that the digital output signals from the adders 16-1 to 16-4 are supplied to terminals A of digital comparators 29-1 to 29-4. The threshold voltage $V_{TH}$ at the terminal 8 is applied in common to terminals B of the comparators and the normal direction signals I, II, III and IV are produced by the comparators depending on the comparison results of the levels at the terminals A and B. The threshold $V_{TH}$ is selected such that only high level signals of the signals generated by the edges are extracted.

Thus, the respective patterns represent the directions I, II, III and IV of the pattern.

The major classifying circuit is now explained for the classes 1, 2, ... with reference to FIGS. 14 and 15A to 15E.

FIG. 14 shows a first classifying circuit for the major class 1 (FIGS. 11 and 12). In the class 1, no normal direction signal is generated as shown in FIGS. 11 and 12 and the sum of the binary signals in the respective directions in the circuit of FIG. 13A or 13B is equal to zero. Accordingly, it may comprise an adder 201 and a comparator 202, and the threshold of the comparator is set to "0" so that the comparator produces an output when the input thereto is equal to the threshold. This output is designated by (A).

Figure 15A:
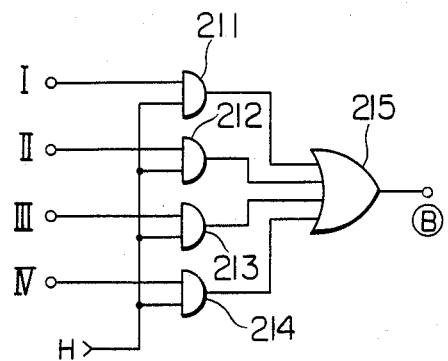
FIGS. 15A to 15E show circuits for generating classifying signals for major classes 2 to 5.

FIGS. 15A to 15E show classifying circuits for the classes 2 to 5. FIG. 15A corresponds to the major class 2, FIG. 15B corresponds to the major class 3, FIG. 15C corresponds to the major class 4, FIG. 15D corresponds to the major class 5 in which the normal direction signals in any three directions are simultaneously generated (class 5-1), and FIG. 15E corresponds to the major class 5 in which the normal direction signals in four directions are simultaneously generated (class 5-2).

Figure 15B:
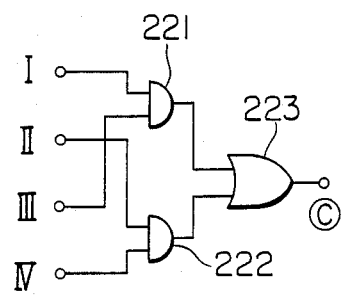
Figure 15C:
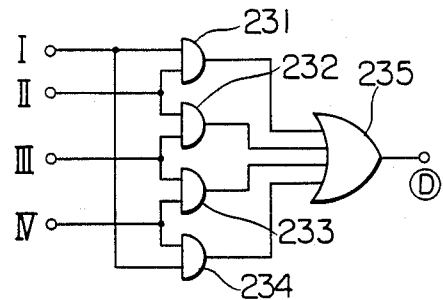
Figure 15D:
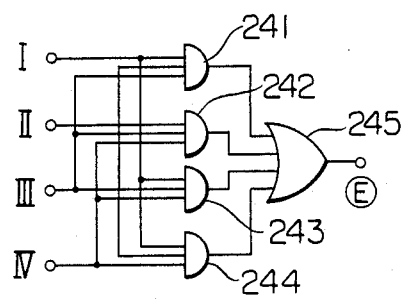
Figure 15E:
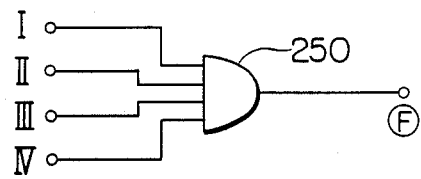

In FIG. 15A, numerals 211 to 214 denote AND gates, numeral 215 denotes an OR gate and H denotes a high level logical signal. In FIG. 15B, numerals 221 and 222 denote AND gates, and numeral 223 denotes an OR gate. In FIG. 15C, numerals 231 to 234 denote AND gates and numeral 235 denotes an OR gate. In FIG. 15D, numerals 241 to 244 denote AND gates and numeral 245 denotes an OR gate. In FIG. 15E, numeral 250 denotes an AND gate.

Those logics are necessarily derived from FIG. 12. For example, let us consider FIG. 15A. In this case, only one normal direction signal is generated for each pattern orientation on the wafer. There are four basic pattern orientations on the wafer. Accordingly, a logic for selecting a case in which one normal direction signal is generated for any of the four pattern orientations. It is nothing but the logic shown in FIG. 15A. In this manner, the classification signal for the major class 2 is produced. The output is designated by (B). Since this logic cannot discriminate the case where two or more normal direction signals are generated, an inhibit circuit to be described later is required.

The logics for the major classes 3 to 5 are apparent from FIGS. 12 and 15B to 15E. Those outputs are designated by (C), (D), (E) and (F), where (E) is for the class 5-1 and (F) is for the class 5-2.

The classification logics have thus been constructed but they are not sufficient for the intended purpose as described above. For example, considering the class 5-1 (three directions in the class 5 of FIG. 11) and the class 5-2 (four directions in the class 5 of FIG. 11), the class 5-2 is not selected when the class 5-1 is selected but the class 5-1 is selected when the class 5-2 is selected.

Such relations also exist between the classes 5-1 and 4, between the classes 4 and 3 and between the classes 3 and 2. Such problem arises when a larger number of normal direction signals is applied to a logic circuit which is intended for a major class having a smaller number of nomal direction signals.

Figure 16A:
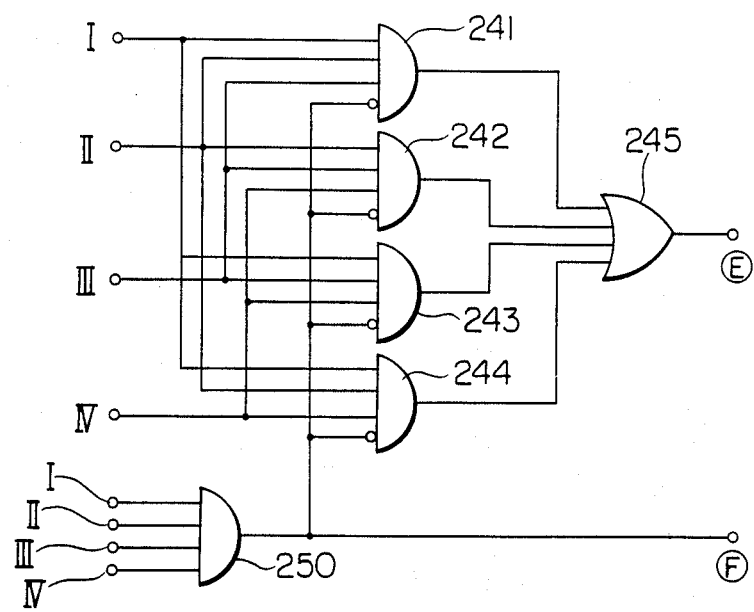
FIGS. 16A and 16B show inhibit circuits for the classifying signals.
Figure 16B:
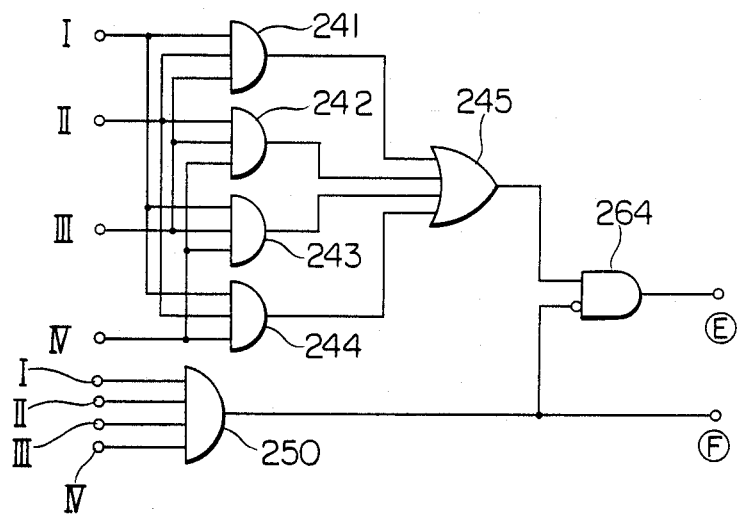

In order to resolve such problems, the output of the class 5-1, for example, is inhibited by the output of the class 5-2 when the class 5-2 is selected. FIGS. 16A and 16B show two inhibition methods to be used between the logic circuits of FIGS. 15D and 15E.

In FIGS. 16A and 16B, logic circuits 241 to 245 and an AND gate 250 are essentially combination of the circuits of FIGS. 15D and 15E. In FIG. 16A, the output signal from the AND gate 250 is used as an inhibit signal to the inputs to the AND gate 241 to 244, and in FIG. 16B, the output signal from the OR gate 245 for the class 5-1 is used as an inhibit signal.

Figure 17:
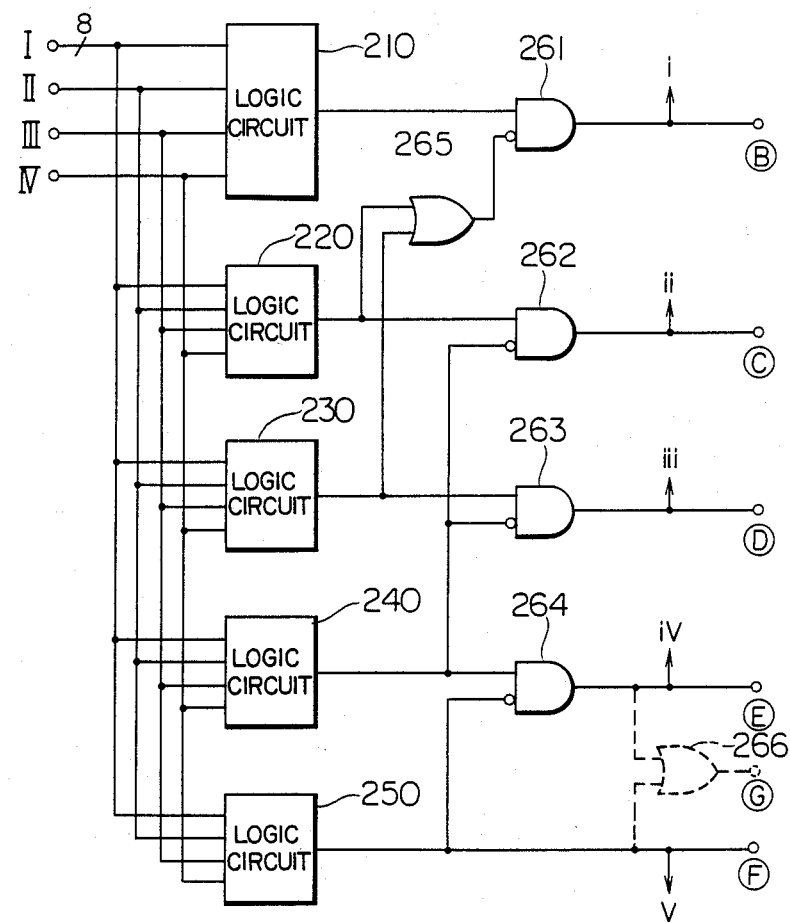
FIG. 17 shows a major-classifying circuit having an inhibit circuit.

In FIG. 17, the inhibit logic shown in FIG. 16B is employed to the logic circuits for all classes.

In FIG. 17, blocks 210 to 250 correspond to the logic circuits shown in FIGS. 15A to 15E, respectively. For example, the block 210 in FIG. 17 corresponds to the logic circuit shown in FIG. 15A. Numerals 261 to 264 denote AND gates and numeral 265 denotes an OR gate. It inhibits the circuit 210 for the major class 2 when the major class 3 or 4 is selected. Classification signals (B) to (E) are the outputs from the logic circuits of FIGS. 15A to 15E, respectively. They are outputted from the AND gates 261 to 264 and 266.

The class 5 should be sub-classified to class 5-1 and 5-2 in generating the inhibit signal. In actual, such sub-classification may not necessary in certain cases. In such cases, an OR gate 266 shown by broken line may be used and an output (G) thereof may be used in place of (E) and (F).

In this manner, six major classification signals (A) to (F) or five major classification signals (A) to (D) and (G) are produced.

Figure 18:
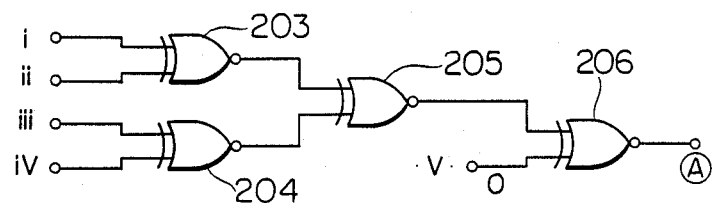
FIG. 18 shows another circuit for generating the classifying signal for the major class 1.

A second embodiment for producing the major classification signal (A) (major class 1) is explained with reference to FIG. 18 (It is noted that the first embodiment is explained with reference to FIG. 14).

In the second embodiment, an output is produced when none of the output signals in FIG. 17 is produced. The output is "1" (or H-level) when the classification signals (A) to (F) are "0" (or L-level). The signals (i) to (v) in FIG. 17 are supplied to EXOR gates 203 to 206 as shown in FIG. 18. The output of the EXOR gate 206 is designated by (A) as is done in FIG. 14.

The major classification of the patterns has thus been described. Sub-classification of the patterns is now explained. In the sub-classification of the patterns, the major classes 2, 3 and 4 of FIG. 11 are sub-divided into two sub-classes, respectively. In the major classification, the high level edge signals in the normal directions are utilized. On the other hand, in the sub-classification, low level normal direction signals which are generated at the round corner by the deviation from the ideal pattern are utilized.

The sub-classification of the patterns is explained with reference to FIG. 19. Vector representation of the reflected diffraction lights in the normal direction and abnormal direction generated by the round corner is shown in FIGS. 5A to 5F. In FIG. 19, major class, subclass, pattern type, number of directions, direction and remark columns are shown in correspondence to FIG. 12. In FIG. 19, the patterns have round corners as opposed to those shown in FIGS. 11 and 12. Names of approximate circles for the round corners are shown at the bottoms of the columns. The number of directions indicates the number of normal direction signals generated by the round corner of the approximate circle associated with the pattern. The directions indicate the directions of the normal direction signals generated by the round corner. Those directions are identical to the directions described above but they are designated by primed reference symbols I', . . . IV' for distinction purpose.

Three major classes 2, 3 and 4 are considered, but other major classes need not be sub-divided. This fact is suggested in FIG. 11.

Let us consider the major class 2. A similarity between sub-classes 2-i and 2-ii is that only one high level signal is generated. On the other hand, a difference between the sub-classes 2-i and 2-ii is the presence or absence of the round corner. As to the number of directions, it is 0 for the sub-class 2-i and 3 for the sub-class 2-ii. Accordingly, if the presence or absence of the normal direction signal due to the round corner can be discriminated, the major class 2 can be sub-divided into the sub-classes 2-i and 2-ii.

Next, let us consider the major class 3. Considering the manner of generation of the normal direction signals generated at the round corners, the number of directions is 1 in one group and 2 in the other group.

Finally, let us consider the major class 4. It can also be sub-divided into a group having the number of directions of 0 and a group having the number of directions of 2.

Sub-classifying signal forming logics are derived from FIG. 19 in the same manner as the major-classifying signal forming logics of FIGS. 15A to 15E are derived from FIG. 12. Prior to the explanation of the logics, it is necessary to form direction signals for the directions I' to IV'. This is now explained with reference to FIGS. 20A and 20B.

Figure 20A:
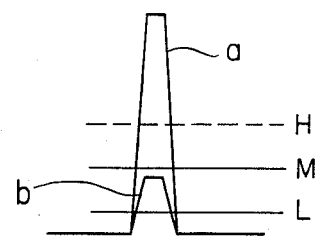
FIGS. 20A to 20B are diagrams which show an analog signal waveform which represents a normal direction signal in one direction by a pulse height and a circuit for generating a normal direction signal generated by the round corner.

FIG. 20A is an analog representation of a pulse height of one of the normal direction signals at the outputs of the circuit shown in FIG. 9A or 9B. Three thresholds, high (H), medium (M) and low (L) are established. A signal A which is larger than the threshold H is used for the major classification (FIGS. 13A and 13B). A signal level by the round corner is low (b in FIG. 20A). The threshold L is established to allow extraction of this signal. The signal larger than the threshold H is not necessary for the formation of the sub-classifying signal. The threshold M lower than the threshold H is established so that a signal between L and M is extracted.

Figure 20B:
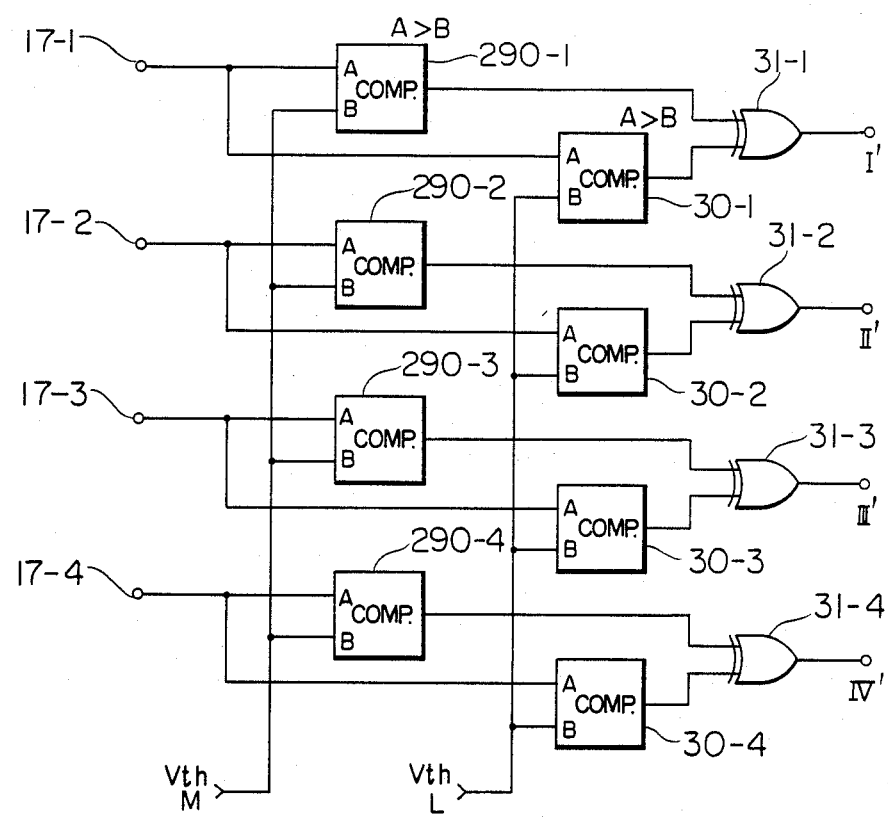

FIG. 20B shows a circuit which selects the signal between the thresholds L and M to form the low level normal direction signal. This circuit is a digital window comparator. Applied to input terminals 17-1 to 17-4 are signals from the output terminals correspondingly designated in FIG. 9A or 9B. Numerals 290-1 to 290-4 and 30-1 to 30-4 denote comparators, and numerals 31-1 to 31-4 denote EXOR gates which produce outputs I' to IV', respectively.

The common threshold M is established for the first group of comparators 290-1 to 290-4, which produce outputs when inputs thereto are higher than the level M. The common threshold L is established for the second group of comparators 30-1, ... 30-4, which produce outputs when inputs thereto are higher than the level L. The outputs from those two groups are supplied to EXOR gates, which produce outputs when inputs thereto are not equal.

When the first group of comparators are constructed to produce the outputs when the inputs thereto are lower than the level M, the EXOR gates 31-1 to 31-4 are replaced by AND gates.

The sub-classifying direction signals are thus formed. The sub-classifying logics are now explained. They may be identical to those shown in FIGS. 15A to 15F.

Patterns having the same directions as those of the sub-class 2-ii of FIG. 19 are searched from FIG. 12 to find the case of the three directions in the major class 5. Accordingly, the corresponding logic is that shown in FIG. 15D. Similarly, the major classes 2, 3 and 4 correspond to the sub-classes 3-i, 3-ii and 4-ii, respectively, and the corresponding logics are those shown in FIGS. 15A, 15B and 15C, respectively. Those are shown in the remark column of FIG. 19.

The relations between the sub-classes and the corresponding circuits are:

| | |
|---|---|
| Sub-class 2-ii | FIG. 15D circuit |
| Sub-class 3-ii | FIG. 15B circuit |
| Sub-class 4-ii | FIG. 15C circuit |

When these circuits are used for sub-classes 2-ii, 3-ii and 4-ii, if one output of these circuits is "0" or low, that means that a pattern under inspection belongs to the sub-class 2-i, 3-i or 4-i. Thus, the major classes 2, 3 and 4 are classified into corresponding two classes.

Figure 21:
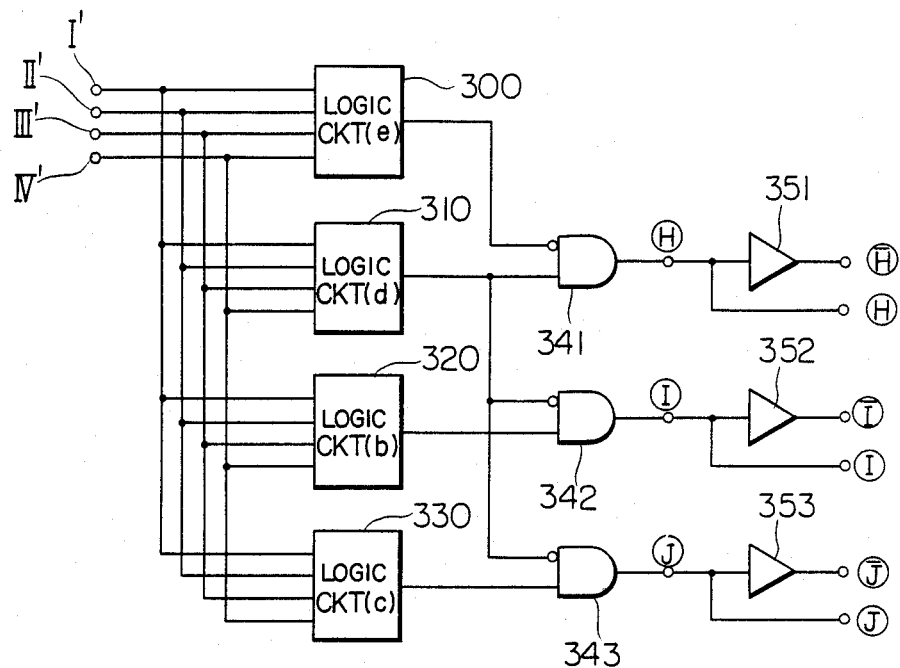
FIGS. 21 and 22 show circuits for generating sub-classifying signals.

It is necessary to inhibit the sub-classifying circuits as are done in FIG. 17. FIG. 21 shows how to inhibit them. The logic circuits in FIGS. 15A to 15E are designated by logics (a), (b), ... (e), respectively. In FIG. 21, numerals 300, 310, 320 and 330 denote the logics (e), (d), (b) and (c). The logic (e) 300 is used only to establish an inhibit state. Numerals 341 to 343 denote AND gates which are inhibited by signals applied to their inverting input terminals. For example, the output of the AND gate 341 is inhibited by the output of the logic (e). The manner of inhibition is exactly opposite to that of FIG. 17.

The outputs of the AND gates 341 to 343 are designated by $\widehat{H}$, $\widehat{I}$ and $\widehat{J}$, respectively. When $\widehat{H}$ is "1" or H (high), it corresponds to the sub-class 2-ii, and when $\widehat{H}$ is "0" or L (low), it corresponds to the sub-class 2-i. To this end, an inverter 351 is used. The same is true for the outputs $\widehat{I}$ and $\widehat{J}$, and inverters 352 and 353 are used. The outputs of the respective inverters are designated by $\overline{\widehat{H}}$, $\overline{\widehat{I}}$ and $\overline{\widehat{J}}$.

Figure 22:
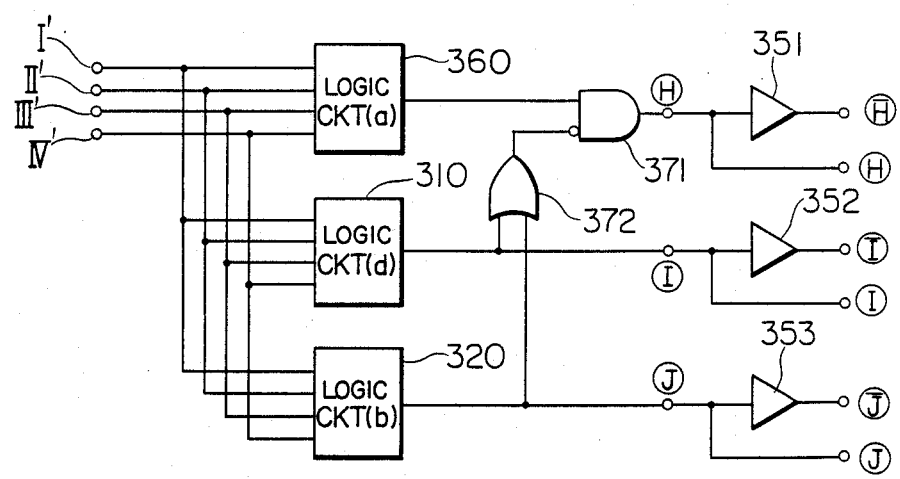

The sub-class 2-ii can be analyzed in a different way. For the semi-circle (½ circle) approximation (FIG. 19, sub-class 2-ii), three normal direction signals by the round corner are generated. It is assumed that the signal along the edge is larger than others. Accordingly, the logic (a) instead of the logic (d) is used. A possible circuit is shown in FIG. 22, in which numeral 360 denotes the logic (a), numeral 371 denotes an AND gate and numeral 372 denotes an OR gate. The like elements to those shown in FIG. 21 are designated by the like numerals.

In FIG. 22, the inhibition is performed in a simple manner. Namely, the logic (a) is inhibited by the outputs of the logics (b) and (c).

In summary, the basic patterns on the wafer are classified into five major classes 1 to 5 and the classifying signals are formed for those major classes. Of those, three major classes 2 to 4 are sub-divided into two sub-classes, respectively, and sub-classifying signals are formed for those sub-classes.

When the wafer is inspected, the pattern shape to which the light beam is irradiated changes from time to time as the light beam is scanned, and one of the classifying signals is selected depending on the shape. Two or more classifying signals are not simultaneously selected.

Nextly, the normal/abnormal discriminators by the first discrination method which are provided one for each of the classification patterns and selectively operated in accordance with the pattern classifying signals formed in the above-mentioned manner are explained.

The input signals (digital) to the normal/abnormal discriminators are the abnormal direction signals which have not been described above. These abnormal direction signals correspond to the abnormal direction light shown in FIG. 7. An abnormal direction signal detector may be a floating threshold type detection circuit similar to a digital floating threshold circuit disclosed in Japanese Patent Application No. 58-176413 filed on Sept. 26, 1983 (not yet laid-open to the public, and hence not prior art) filed by the assignee of the present application. This circuit is now explained.

FIG. 23 shows an example of a detection signal derived from a reflected deffraction light from a pattern. As seen from FIG. 23, the signal produced by scanning by the light beam the wafer having an integrated circuit formed thereon usually includes a pulsating wave (A.C. component) and a pedestal wave (D.C. component), and the D.C. component varies with various conditions and is not constant. In FIG. 23, e-f-g is a signal waveform for one scan period, and the pulsating wave and the pedestal wave are superimposed in the chip pattern area. It is correlated to a relative ratio of an irradiation beam diameter to a pattern size, a scan speed and a time constant of an amplifier. If a defect is present in the pattern, a pulse defect signal h is produced at a time $t_h$ corresponding to the defect position.

A principle of operation of the floating threshold type circuit for detecting such a defect signal is explained with reference to FIGS. 24A to 24D and 25.

FIGS. 24A to 24D show time charts for explaining the principle and an abscissa represents a time t while an ordinate represents a detection signal voltage e(t). A time length t scan taken on the abscissa in those figures is a minimum required unit, for example, a time interval required for one scan in the pattern defect inspection.

FIG. 24A shows a waveform which comprises only a signal of an undesired level such as a background noise. This signal should not be finally outputted as a binary signal or a multi-level signal at any time. FIG. 24B shows a pedestal wave which is a simplified form of the waveform of FIG. 24A. In FIG. 24C, the pedestal waveform of FIG. 24B is sampled at a period of Ts. In FIG. 24D, five samples are extracted at times $t_1$ to $t_5$. The sample at time $t_1$ is represented by $e_1$, the sample at time $t_2$ is represented by $e_2$, and so on.

Assuming that a threshold at the time $t_3$ under consideration is $E_{sh}$, the above requirement is represented by $$E_{sh} > e_3 \tag{1}$$

In order to form the threshold $E_{sh}$ which meets the relation (1), the following operations are performed. An average $\bar{E}$ of $e_j$ (j=1, ... 5) is given by $$\bar{E} = 1/5 \Sigma_j e_j \tag{2}$$

A threshold $E'_{sh}$ is defined as follows.

$$E'_{sh} = \bar{E} + (\bar{E} - E_{min}) \tag{3}$$

where $E_{min}$ is minimum one of $e_j$. When $E'_{sh}$ is used as the threshold at the time $t_3$, there occurs two cases $$E'_{sh} \geq e_3 \tag{4}$$

that is, $E'_{sh} > e_3$ and $E'_{sh} = e_3$.

In FIG. 24D, the average $\bar{E}$ is shown by a horizontal broken line, the minimum $E_{min}$ of $e_j$ is $e_1$, the difference ($\bar{E} - E_{min}$) is shown by a double-head arrow above $e_1$, and $E'_{sh}$ is shown by a horizontal solid line above $e_3$ at the time $t_3$.

A time point which is one sampling period $T_s$ after the time $t_5$ is defined as a time $t_6$ (not shown). At this moment, the time under consideration changes from $t_3$ to $t_4$, the average $\bar{E}$ and the minimum $E_{min}$ are updated accordingly, and $E'_{sh}$ is also updated. A time which is one sampling period $T_s$ after the time $t_6$ is defined as a time $t_7$ (not shown). The time under consideration now changes from $t_4$ to $t_5$, $\bar{E}$ and $E_{min}$ are updated and $E'_{sh}$ is changed. In this manner, the threshold $E'_{sh}$ is sequentially formed as the time elapses.

Figure 25:
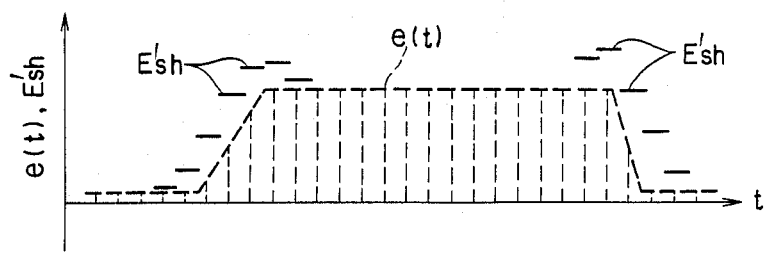
FIG. 25 is a diagram which illustrates the formation of the threshold in the floating threshold circuit.

FIG. 25 shows the formation of the threshold. A rising slope and a falling slope of the pedestal wave have different gradients from each other as do in FIGS. 24C and 24D. In FIG. 25, the thresholds $E'_{sh}$ are shown by horizontal solid lines having a length equal to the time interval $T_s$. As seen from FIG. 25, the thresholds are formed in accordance with the gradients of the rising slope and the falling slope of the pedestal.

As seen from FIG. 25, the threshold $E'_{sh}$ defined by the formula (3) satisfies the formula (4). Namely, there occurs a case where $E'_{sh} = e_3$ holds as well as a case where $E'_{sh} > e_3$ holds. In this case, $E'_{sh}$ is not established as the threshold. Accordingly, it is necessary that the formula (1) is always met.

In order to meet the formula (1), a real number $\alpha$ which is defined below may be introduced.

$$E_{sh} = \bar{E} + (1+\alpha)(\bar{E} - E_{min}) \tag{5}$$

The value $\alpha$ may be set in a range of $0 < \alpha < \infty$ or it may be variable. The introduction of $\alpha$ corresponds to a level-up of $E'_{sh}$ and, by using $E_{sh}$ thus obtained, the formula (1) is met.

In accordance with the threshold formation represented by the formula (5), the threshold varies with the change of the signal of the undesired level so that the defect signal (or abnormal signal) is stably extracted and is stably binarized or digitized against the variation of the D.C. component.

Figure 26:
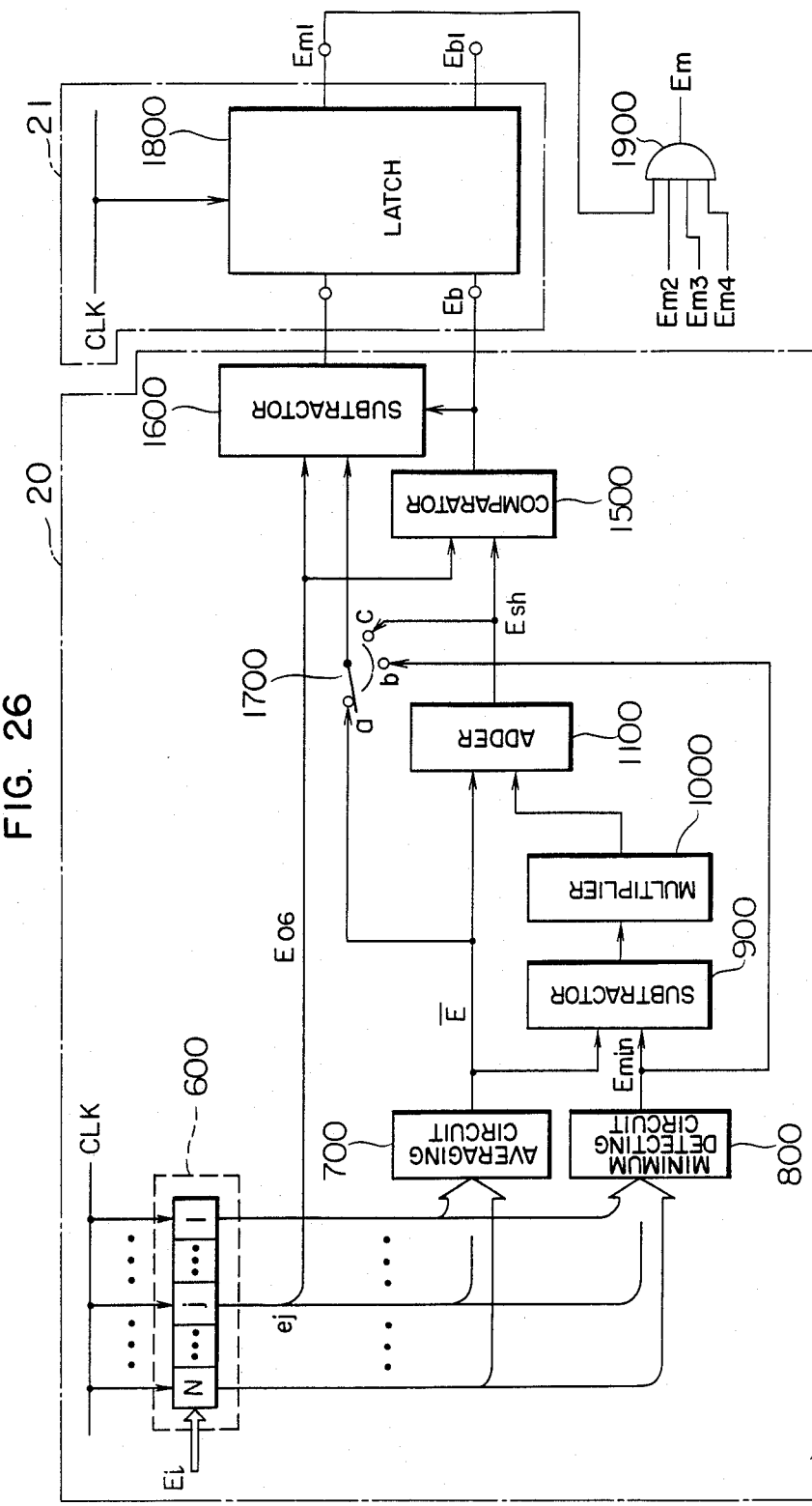
FIG. 26 shows a floating threshold type detection circuit and an abnormal signal extraction circuit used to detect an abnormal signal.

FIG. 26 shows a block diagram of a floating threshold type detection circuit which implements the threshold formation technique described above. It comprises a shift register 600 which includes a plurality of shift registers connected in series which are temporary storages, an averaging circuit 700, a minimum detection circuit 800, a subtractor 900, a multiplier 1000, an adder 1100, a comparator 1500, a subtractor 1600 and a switch 1700. An input signal Ei to the shift register 600 is produced by converting the samples at the respective times shown in FIGS. 24C and 24D to a multi-value digital signal having an appropriate resolution by an A/D converter (for example, 14-1 in FIG. 9B). As the input signal Ei, for example, the digital signal appearing at the terminal 17-1 of FIG. 19B for the reflected diffraction lights in the abnormal direction is used. The circuit of FIG. 26 is provided for each of the signals from other terminals 17-2, 17-3 and 17-4. The outputs $E_{m1}$–$E_{m4}$ of respective circuits are inputted to an AND gate 1900 and the output ($E_m$) of the AND gate is inputted to an normal/abnormal discriminator shown in FIG. 28 so as to be used for determining whether a pattern under inspection is defective or not.

The shift register 600 serially stores the time-serial input signals $E_i$ one for each of the serially-connected stages 1 ... j ... N and can parallely read out the stored content. The reading and writing of the shift register 600 are controlled by a clock pulse CLK which determines a period of A/D conversion of the input signal. The number N of stages of the shift register is odd (3, 5, 7, ... ) and the shift register j for the time under consideration is a central stage. Thus, when N=3, 5, 7, ... , j=2, 3, 4, .... In the above description of the threshold formation, N=5 and j=3.

The averaging circuit 700 calculates an average $\bar{E}$ of N digital signals $e_j$ read from the shift register 600. It comprises an adder and a divider. The former can be readily constructed by a conventional binary adder. The former is complex in hardware configuration if it is constructed by a conventional divider because of division by the odd number N=3, 5, 7, .... In order to resolve this problem, a read-only memory (ROM) may be utilized.

The division by ROM is briefly explained. The bits of the otuput of the adder and the bits of the divider N are paired to designate memory addresses. Quotients are previously stored at the respective addresses. Thus, the memory address is designated in accordance with the output of the adder and the quotient is read from the memory at the selected address.

The minimum detection circuit 800 detects a minimum $E_{min}$ of the N digital signals $e_j$ read from the shift register 600. It may be readily constructed in accordance with a tournament comparison method and hence the explanation thereof is omitted.

The subtractor 900, multiplier 1000, adder 1100, comparator 1500 and subtractor 1600 may be any circuits having the respective operation functions and the constructions thereof are not explained here. Only the operations to be performed are explained. The subtractor 900 subtracts the output $E_{min}$ of the minimum detection circuit 800 from the output $\bar{E}$ of the averaging circuit 700. The multiplier 1000 multiplies the output $(\bar{E}-E_{min})$ of the subtractor 900 by a constant $(1+\alpha)$, and the adder 1100 adds the output $\bar{E}$ of the averaging circuit 700 to the output $(1+\alpha)\cdot(\bar{E}-E_{min})$ of the multiplier 1000 so that the threshold $E_{sh}$ represented by the formula (5) is produced in a digital form.

Since the processing time of the averaging circuit 700, minimum detection circuit 800 and blocks 900, 1000 and 1100 is several hundreds of nanoseconds at most, the threshold $E_{sh}$ can be formed in substantially real time. Thus, the threshold $E_{sh}$ can be formed before the arrival of the next clock pulse. Accordingly, at each arrival of the clock pulse, the content of the shift register 600 is updated and the values $\bar{E}$, $E_{min}$ and $E_{sh}$ are updated. On the other hand, the value $e_j$ read from the central stage is outputted from the threshold circuit as a signal $E_{ob}$ which is to be compared with the threshold $E_{sh}$.

The comparator 1500 compares the signal $E_{ob}$ with the threshold $E_{sh}$ and produces an output if $E_{ob} \leq E_{sh}$ and no output if $E_{ob} \geq E_{sh}$. It determines if the signal $E_{ob}$ is an abnormal signal. The output of the comparator 1500 is designated by $E_b$.

The detection of the defect signal pulse h shown in FIG. 23 is now explained with reference to FIGS. 26 and 27.

Figure 27:
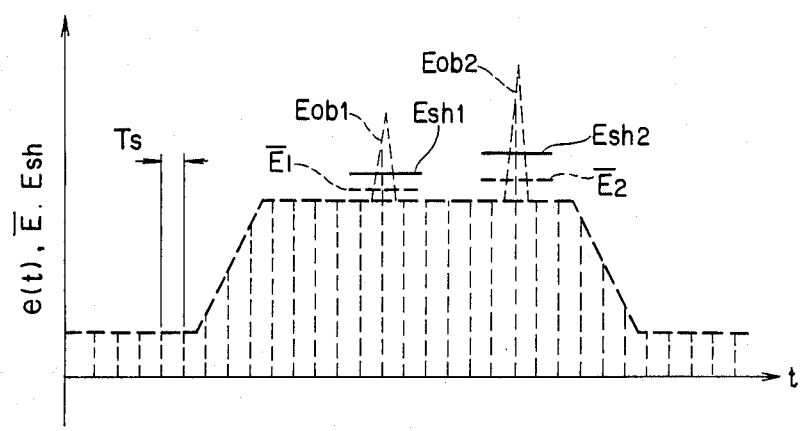
FIG. 27 is a diagram which illustrates the formation of the threshold and the detection of the abnormal signal by the circuit of FIG. 26.

In FIG. 27, a first defect signal pulse, a threshold at that moment and an average are represented by $E_{0b1}$, $E_{sh1}$ and $\bar{E}_1$. The values for a second defect signal pulse are represented by $E_{0b2}$, $E_{sh2}$ and $\bar{E}_2$. Relations of $E_{0b1} > E_{sh1} > \bar{E}_1$ and $E_{0b2} > E_{sh2} > \bar{E}_2$ exist between those values as a result of the threshold formation method described above. While the A.C. component is omitted in FIG. 27, it is apparent from the formula (5) that the threshold floats effectively even when the A.C. component is included.

In FIG. 26, numeral 1600 denotes a subtractor which is timed by the binary output from the comparator 1500 and numeral 1700 denotes a switch which selects one of the average $\bar{E}$ at a contact a, the minimum $E_{min}$ at a contact b and the threshold $E_{sh}$ at a contact c and supplies the selected one to one input of the subtractor 1600 which receives the signal $E_{ob}$ at the other input. In this manner, any one of $E_{ob}-\bar{E}$, $E_{ob}-E_{min}$ and $E_{ob}-E_{sh}$ is produced as the multi-value output $E_{m1}$.

The switch 1700 may be of any type so long as it performs the above functions.

A latch 1800 shown in FIG. 26 constitutes the abnormal signal extraction circuit 21 shown in FIG. 7.

The latch 1800 is a temporary storage which is controlled by the clock pulse CLK. It transfers the binary output $E_b$ of the comparator 1500 or the multivalue output $E_{m1}$ of the subtractor 1600.

The output $E_b$ may be utilized as a defect/nondefect signal when only the presence or absence of the defect is necessary, or as a timing signal or gate signal for the presence or absence of the defect. The other output $E_m$ ($E_{m1}-E_{m4}$) reserves the magnitude of the defect. At this stage, it is not clear whether these signals are fatal defects to the device function. It is determined in the next stage.

The floating threshold type circuit is connected to each of the output terminals 17-1 to 17-4 of the abnormal direction in FIG. 9A or 9B. A signal which is abnormally large as compared with a predetermined level in the abnormal direction due to the pattern defect (broken line, shoft circuit, etc.) or deposition of foregin material is detected. This signal includes the affect by the round corner, as described above. The normality/abnormality of the detected abnormal direction signal is determined.

The normal/abnormal discriminator is explained with reference to FIGS. 28 to 30B.

Figure 28:
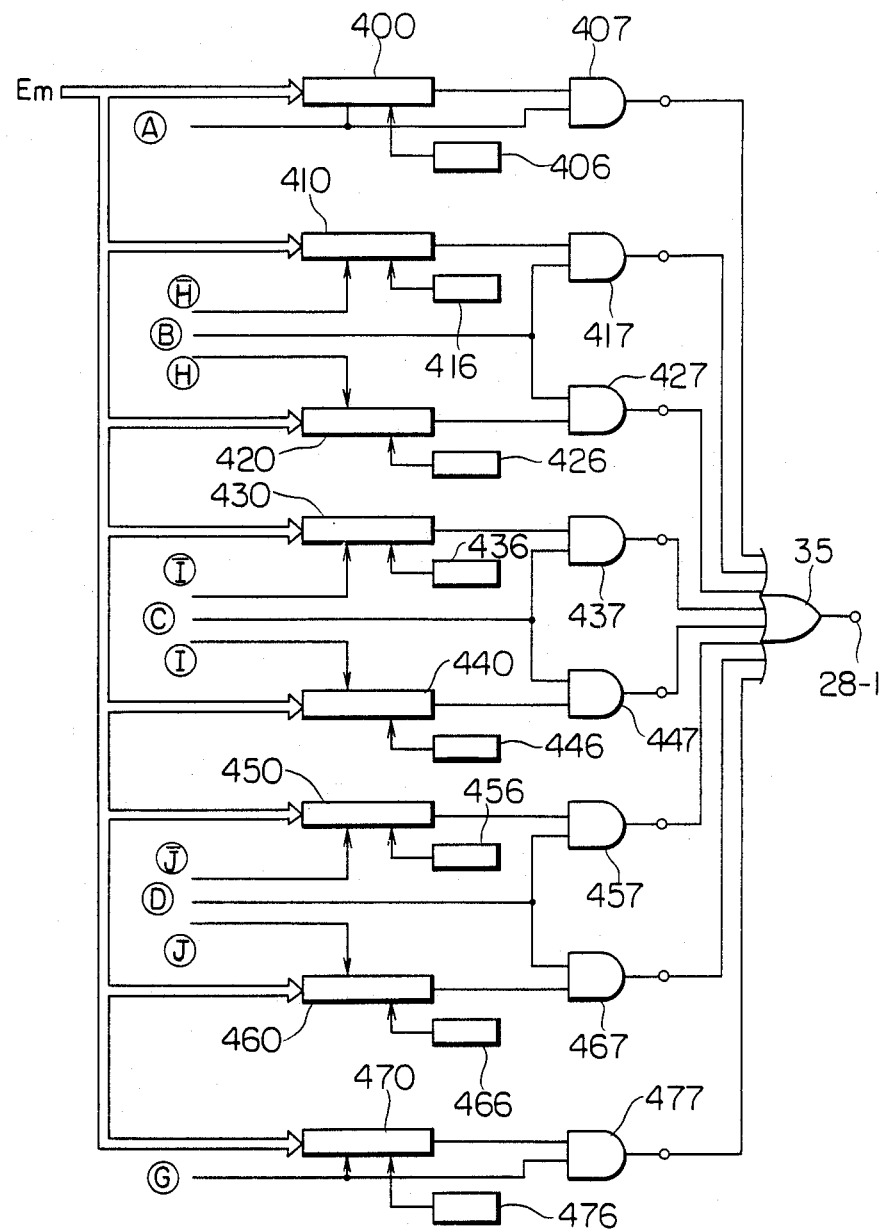
FIG. 28 is a block diagram of a normal/abnormal discriminator.

Referring to FIG. 28 which shows a block diagram of the discriminator, the overall operation is explained. As described above, the patterns formed on the wafer are classified into eight classes including the basic patterns and the composite patterns. Eight normal/abnormal discriminators are provided one for each of those classes. The discriminators receive a common input. The input is the multi-value output $E_m$ of the abnormal direction signal extraction circuit having the floating threshold type detection circuit shown in FIG. 26. The class of the pattern to which the extracted abnormal direction signal belongs is determined by the circuits shown in FIGS. 17, 18 and 21 or 22, which generate the classifying signals Ⓐ to Ⓙ. Those classifying signals are used as gate signals to activate the corresponding discriminators.

In FIG. 28, numerals 400, 410, 420, 430, 440, 450, 460 and 470 denote discriminators for the classes 1, 2-i, 2-ii, 3-i, 3-ii, 4-i, 4-ii and 5, respectively. The respective discriminators have independently adjustable threshold setting circuits 406, 416, 426, 436, 446, 456, 466 and 476. Numerals 407, 417, 427, 437, 447, 457, 467 and 477 denote AND gates.

The pattern classifying signals Ⓐ to Ⓓ, Ⓖ, Ⓗ to Ⓙ and Ⓗ to Ⓙ are applied to the circuit of FIG. 28 as shown. Let us assume that the classifying signal for the class 2-ii is generated in the pattern inspection and other classifying signals are not generated. As a result, the discriminator 420 operates. The abnormal direction signal $E_m$ due to the round corner is detected and it is applied to the discriminator 420. Since this signal is due to the semicircle approximation round corner and is not a true defect signal, the threshold setting circuit 426 is selected such that no output is produced by the discriminator 420.

In this manner, the discriminators can discriminate independently from each other. The outputs from the AND gates 407, 417, . . . are supplied to the OR gate 35 which produces a final true defect signal at a terminal 28-1.

Figure 29:
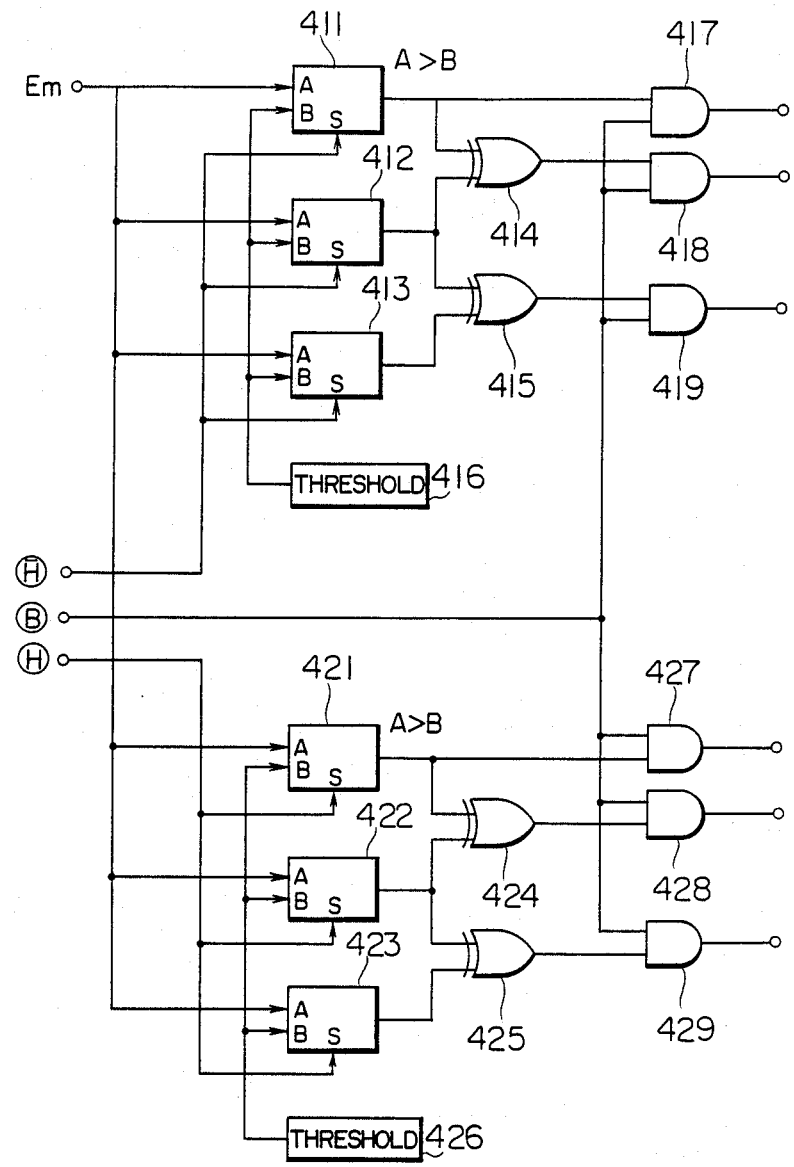
FIG. 29 shows a circuit for discriminating normality/abnormality and sizing the defect.

Representative ones of the blocks shown in FIG. 28 are explained in detail. FIG. 29 shows the discriminator for the major class 2. The upper half thereof is for the sub-class 2-i and the lower half is for the sub-class 2-ii. The upper half corresponds to the blocks 410, 416 and 417 of FIG. 28 and the lower half corresponds to the blocks 420, 426 and 427. In FIG. 29, numerals 411 to 413 and 421 to 423 denote comparators, numerals 416 and 426 denote digital threshold setting circuits, numerals 414, 415, 424 and 425 denote EXOR gates and numerals 417 to 419 and 427 to 429 denote AND gates. The upper comparators are activated by the sub-classifying signal (H) and the lower comparators are activated by the sub-calssifying signal (H̄). The major classifying signal (B) is supplied to the upper and lower AND gates as a gate signal to the output of the EXOR gates.

The upper half of the circuit of FIG. 29 is explained. The upper ones of the three comparators have higher thresholds than the lower ones. The threshold for the comparator 413 is higher than the level of the abnormal direction signal generated by the round corner so that the round corner is not detected.

This theory is applicable to the discriminators of all other classes of basic patterns. The thresholds for the discriminators can be independently set and they may be set in accordance with the specific patterns classified. The second and third comparators are provided to size the detected defect signal (The abnormal direction signal at this stage may be regarded identical to the defect signal). In FIG. 29, three-level sizing is effected.

Figure 30A:
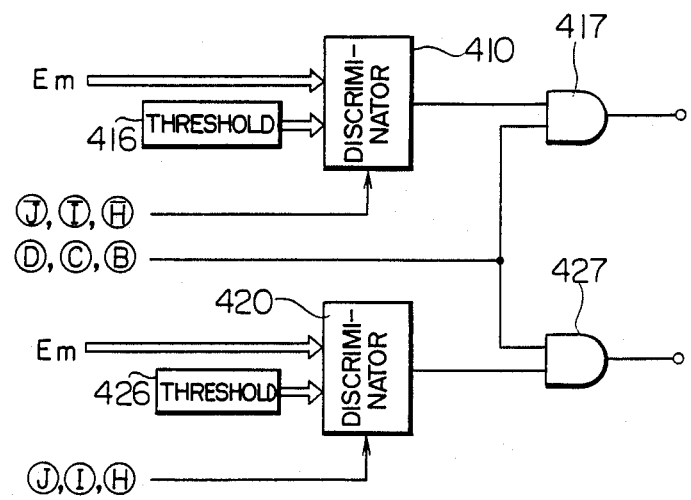
FIGS. 30A and 30B show block diagrams of the circuit of FIG. 29.

FIG. 30A shows a block diagram of the discriminator for the major class 2 shown in FIG. 29. Numeral 410 denotes a block which includes three comparators and two EXOR gates 411 to 415, and numeral 417 denotes a block which includes the AND gates 417 to 419.

Figure 30B:
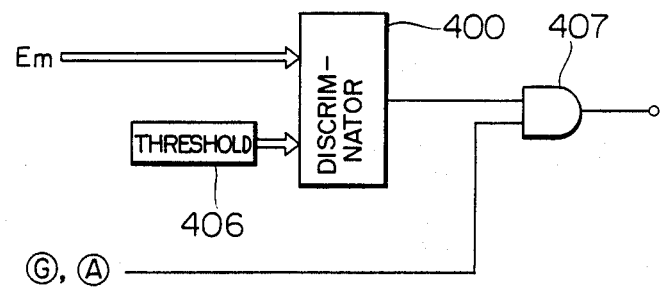

FIG. 30B shows a block diagram of the discriminator for the major class 1. The discriminators for other major classes 3 and 4 are similar to that shown in FIG. 30A. In this case, the major classifying signal (C) or (D) is applied in place of (B), the sub-classifying signal (I) or (J) is supplied in place of (H) and the sub-classifying signal (Ī) or (J̄) is supplied in place of (H̄).

The discriminator for the class 5 is similar to that shown in FIG. 30B. In this case, the major classifying signal (G) is supplied in place of (A).

FIG. 28 shows the overall block diagram of the discriminators based on FIGS. 30A and 30B. In FIG. 28, eight discriminators are used and the outputs thereof are supplied to the OR gate 35 which produces the final defect signal (including information on the defect size).

As described above, the discriminators for discriminating the normality/abnormality of the detected abnormal direction signals are provided for each pattern class, and the discrimination levels of the discriminators can be independently set. Accordingly, only the signals discriminated as abnormal are outputted as the defect signals, and the sizing thereof is easily attained.

Figure 31:
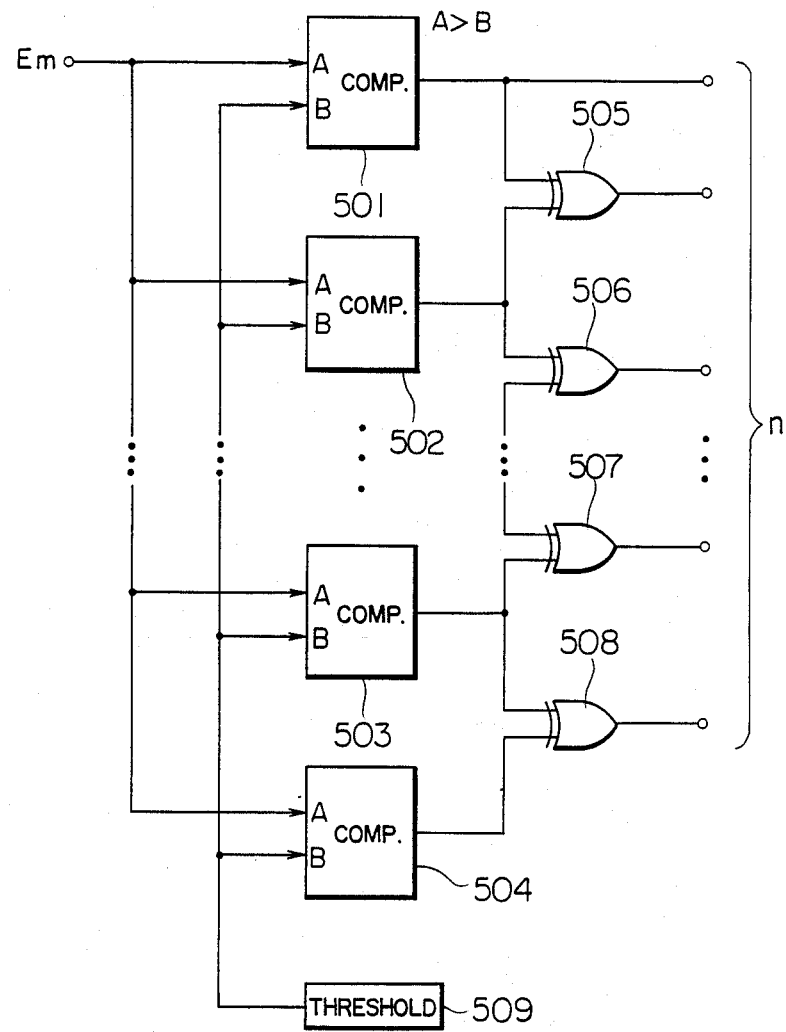
FIG. 31 shows a circuit for sizing the defect signal.

While the three-level sizing of the defect signal is shown in FIG. 29, any number of level-sizing can be attained by expanding the method shown in FIG. 29. FIG. 31 shows only one discriminator. Numerals 501 to 504 denote n comparators and numerals 505 to 508 denote n-1 EXOR gates.

Figure 32:
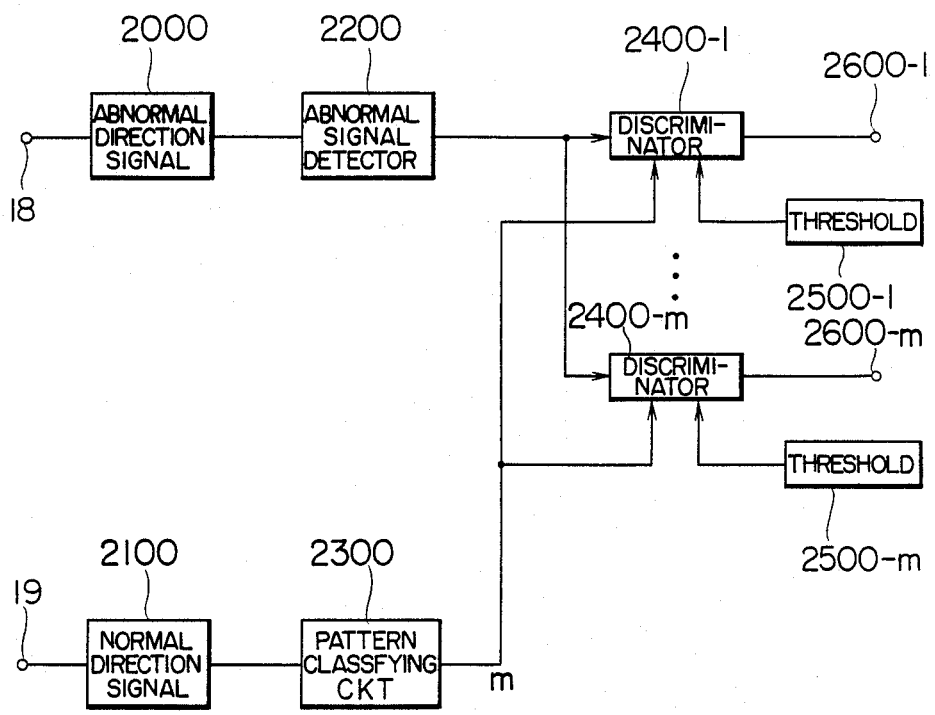
FIG. 32 is a block diagram of the present invention.

FIG. 32 shows a block diagram of the overall system in accordance with the first method of the present invention. It shows a block diagram of the defect signal extraction circuits shown in FIG. 6. Applied to an input terminal 18 are the outputs of the abnormal direction detectors (even-numbered detectors in FIG. 8B) of the detectors 106, and applied to an input terminal 19 are the outputs of the normal direction detectors (odd-numbered detectors in FIG. 18B). Numerals 2000 and 2100 denotes circuits for generating the digital abnormal direction signals and normal direction signals based on the input signals, and correspond to the circuits shown in FIGS. 9A and 9B. Numeral 2200 denotes the abnormal signal detector which uses the floating threshold type detection circuit. Numeral 2300 denotes a pattern classifying signal which includes the major-classifying circuit shown in FIG. 17 and the sub-classifying circuits shown in FIGS. 21 and 22. Numerals 2400-1 to 2400-m denote m normal/abnormal discriminators shown in FIG. 28. Numerals 2500-1 to 2500-m denote m threshold setting circuits which establish independent thresholds to the m normal/abnormal discriminators.

To summarize the operation heretofore described, with reference to FIG. 32, the outputs of the detectors in the abnormal direction and the normal direction, applied to the input terminals 18 and 19 are supplied to the circuits 2000 and 2100 respectively, which produces the digital abnormal direction signals and normal direction signals. The abnormal direction signals are applied to the abnormal signal detector 2200 which uses the floating threshold type detection circuit so that only the abnormal signals larger than a predetermined level are detected.

On the other hand, the normal direction signal is applied to the pattern classifying circuit 2300 in which m pattern classifying signals for major classes and subclasses are produced. One of m normal/abnormal discriminators corresponding to the input signal pattern is selected by the pattern classifying signal. The detected abnormal signal is supplied to the normal/abnormal discriminators 2400-1 to 2400-m and the selected one of them discriminates the normality/abnormality. If the abnormal signal is determined to be due to the round corner, no output is produced, and only the signal due to the true defect is sized and outputted. The normality/abnormality discrimination depends on the threshold. The class of the pattern changes from time to time during the inspection of the wafer and the active normal/abnormal discriminator changes from time to time accordingly. The discrimination results are outputted from the output terminals 2600-1 to 2600-m and sent to an OR gate in the same way as FIG. 28 and the output of the OR gate is sent to the signal processing circuit 112 of FIG. 6.

The above method for dscriminating the abnormal signal in the pattern defect inspection apparatus includes certain problems. The block 260 in FIG. 7 is provided to resolve those problems. Reference numeral 28-3 denotes the output of the block 260. The above problems and means for resolving the problems (the circular pattern discriminator) are now explained.

Circular Pattern Discriminator

Figure 33A:
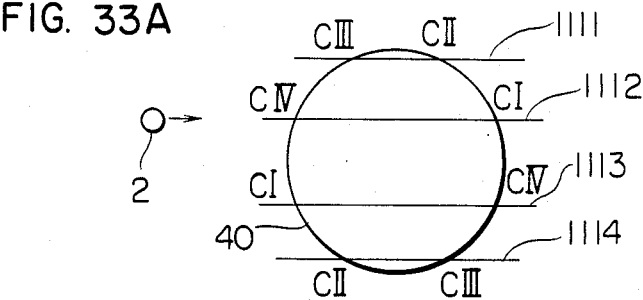
FIGS. 33A and 33B are diagrams which illustrate the generation of the reflected diffraction lights in a circular pattern inspection.
Figure 33B:
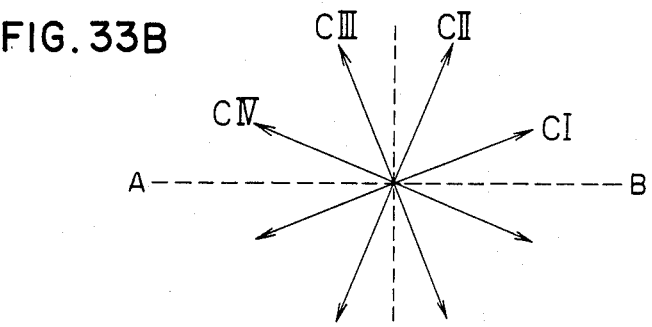

FIG. 33A illustrates a circular pattern 40 and the scan thereof by a laser beam 2. FIG. 33B illustrates the directions in which the laser beam is reflected. As the laser beam 2 is scanned over the circular pattern 40 along lines 1111 to 1114, the reflected diffraction lights from the circular pattern have high intensity levels in a direction of CIII at a point CIII at which the laser beam intersects the circular pattern, in a direction CII at a point CII, in a direction CIV at a point CIV, and in a direction CI at a point CI. Those directions are abnormal directions in the arrangement of the detectors shown in FIG. 8B. Thus, when the apparatus of FIG. 32 is used, the circular pattern is detected as the defective pattern. The circuit of FIG. 34 can discriminate a false defect pattern and a true defect pattern. As seen from FIGS. 32, 33A and 33B, if the directions of the reflected diffraction lights generated when the circular pattern 40 is scanned by the laser beam 2 along the lines 1111 to 1114 are defined as shown in FIG. 33B, the directions of the reflected diffraction lights by the pattern edges regularly change in a manner of CIII→CII, CIV→CI, CI→CIV and CII→CIII. Thus, a circuit of FIG. 34 determines the circular pattern if such regularity is detected to prevent the circular pattern from being erroneously detected as the defect pattern.

Figure 34:
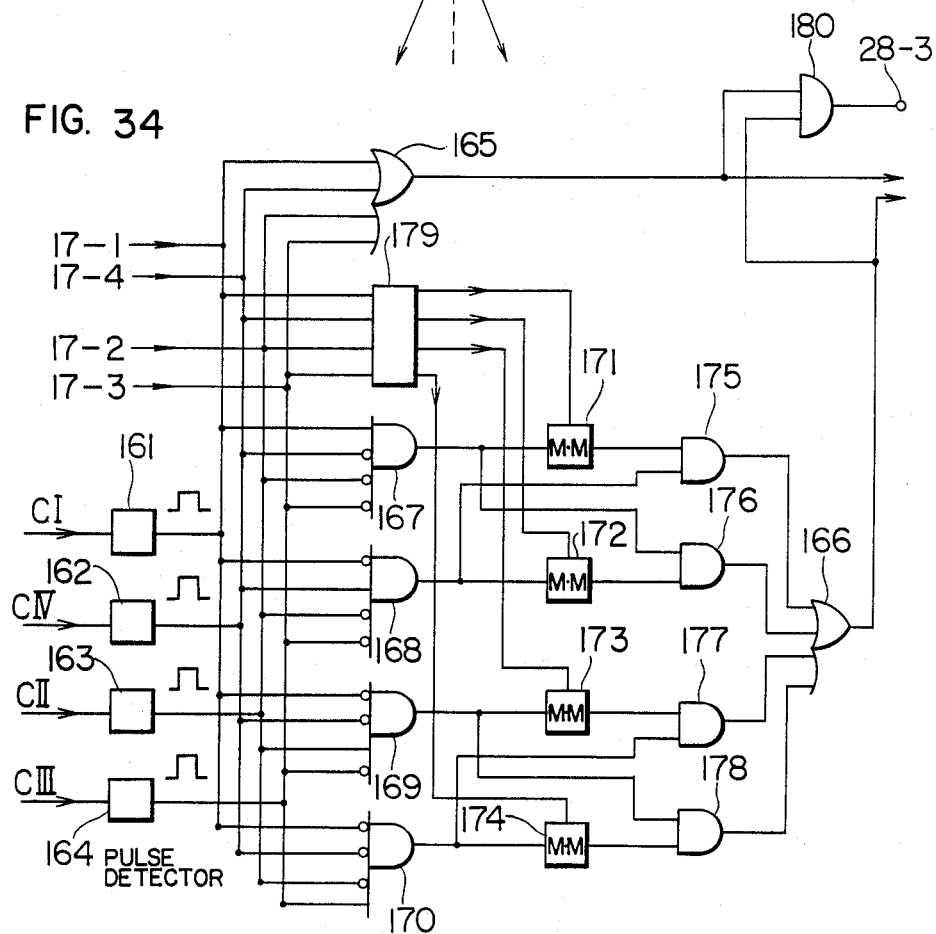
FIG. 34 shows a signal processing circuit for a circular pattern.

FIG. 34 shows a processing circuit for signals from the detectors arranged in the abnormal directions (for example, 11-2 and 11-10, 11-4 and 11-12, 11-6 and 11-14, and 11-8 and 11-16 in FIG. 8B). Numerals 161 to 164 denote pulse detectors. Input signals CI, CIV, CII and CIII thereto are combinations of the opposing signals from the detectors 11-2 and 11-10, 11-8 and 11-16, 11-4 and 11-12, and 11-6 and 11-14 in FIG. 9B. The signals CI, CIV, CII and CIII are analog. They are digitized in the pulse detectors 161 to 164 and pulses are detected thereby. Instead of using 161 to 164, the signals from the terminals 17-1, 17-4, 17-2 and 17-3 in FIG. 9A or 9B may be used. If a pulse is included in the analog signal, a high level signal of a predetermined width is outputted.

When the circular pattern is scanned, the pulses by the reflected diffraction lights generated at the edge are generated in the sequence of CI→CIV, CIV→CI, CII→CIII or CIII→CII. If the pulses are generated in this sequence, a gate 166 produces a high output. The outputs from the gates 166 and 165 are supplied to a microcomputer which, when the output of the gate 166 is high, determines that the high data and the immediately previous data of the abnormal signal data detected during the scan by the laser beam are due to the circular pattern and are not due to the defect pattern.

In many cases, the pulses caused by the defect pattern are generated in many directions simultaneously, but if the diameter of the circular pattern is sufficiently larger than the laser beam diameter, the pulses are generated only in one direction because the edge of the circular pattern scanned by the laser beam can be regarded as a straight line. This is detected by AND gates 167, 168, 169 and 170. Numerals 171, 172, 173 and 174 denote monostable multivibrators which are triggered by the outputs of the gates 167, 168, 169 and 170 to produce positive pulses of a predetermined duration T which is determined by the scan speed of the laser beam and the diameter of the circular pattern. It corresponds to a time required for the laser beam to scan about 90% of the diameter of the circular pattern. The diameter of the circular pattern depends on the integrated circuit to be inspected. This pulse corresponds to the time points at which two signals are generated by the circular pattern and an upper limit of a distance on the pattern corresponding to the time difference between those two signals. For example, if the pulse is generated only in CI and the pulse is then generated in CIV within a predetermined time period, the outputs of the gates 175 and 166 are high and the circular pattern is detected. This is explained with reference to the drawing. FIG. 35 shows signal waveforms of the circuit of FIG. 34 when the circular pattern is scanned by the laser beam along the line 1113. FIG. 35(a) shows the output waveform of the pulse detector 161, which is the pulse signal generated at the point CI on the circular pattern 40, and FIG. 35(b) shows the output waveform of the pulse detector 162, which is the pulse signal generated at the point CIV on the circular pattern 40. The monostable multivibrator 171 is triggered by the pulse of FIG. 35(a) to produce a pulse of a predetermined duration T as shown in FIG. 35(c). The waveforms of FIGS. 35(b) and 35(c) are supplied to the AND gate 175 which produces "1" output at the same time as the pulse of FIG. 35 (b) is generated. The "1" output of the AND gate 175 is supplied to the OR gate 166 which "1" output. The output of the OR gate 166 is supplied to a logic circuit (not shown) which determines that the two pulse signals (FIG. 35(e)) corresponding to the pulses of FIGS. 35(a) and 35(b), outputted from the OR gate 165 are due to the circular pattern. Alternatively, the outputs of the OR gates 165 and 166 are ANDed by an AND gate 180 and the output thereof is used as a defect signal. A circuit 179 clears the outputs of the monostable multivibrators 171, 172, 173 and 174 in the following cases. In other words, the patterns are not circular patterns in the following cases (1) to (4). (1) When two or more outputs of the pulse detectors 161, 162, 163 and 164 are high, all of the monostable multivibrators 171, 172, 173 and 174 are cleared. (2) When one of the outputs of the pulse detectors 161 and 162 is high and then one of the outputs of the pulse detectors 163 and 164 is high, the active one of the monostable multivibrators 171 and 172 is cleared. (3) When one of the outputs of the pulse detectors 163 and 164 is high and then one of the outputs of the pulse detectors 161 and 162 is high, the active one of the monostable multivibrators 173 and 172 is cleared. (4) If the pulses are successively generated at the same output, for example, when the output of the pulse detector 161 is high and then the same output is again high, the monostable multivibrator 171 is cleared.

The present embodiment is implemented by hardwares. Alternatively, the four input signals to the OR gate 165 may be directly supplied to a computer to determine the circular pattern based on the read-in times of the data and the contents of the data.

The true pattern defect signal is produced based on the above signals and it is ANDed with the output signal 28-1 and 28-2 from the first and second normal/abnormal discriminator described above. The block 260 shown in FIG. 7 prevents the circular pattern from being erroneously detected as the defect pattern and numeral 28-3 denotes a circular pattern discrimination signal from the circuit 260.

In accordance with the present embodiment, the circular pattern which has been heretofore erroneously detected as the defect pattern is detected as a normal pattern and the reliability of the defect inspection apparatus is improved.

Second Determination Method

The nomral/abnormal discriminator by the second determination method is already shown by the blocks 25, 26 and 28-2 in FIG. 7.

A basic concept of the present determination or discrimination method is first explained.

The following first discriminating circuit is provided. That is, since the intensity of the reflected diffraction lights in the abnormal directions by the roundness created by the limit of the performance of the lithography is limited, the pattern is determined as the defective pattern if the sum of the abnormal direction signals is larger than an appropriate threshold given from outside.

If the sum is smaller than the threshold, the second discrimination circuit is used. The reflected diffraction lights in the normal directions which are as strong as those in the abnormal directions are generated because of the roundness.

The following explanation which was basically described earlier is again presented for better understanding of the invention. FIGS. 36 and 37 show a pattern 35 having right angle crossing edges and a pattern 45 having 45° crossing edges. Corners thereof are rounded. The reflected diffraction lights newly generated by the round corner in addition to the inherent reflected diffraction lights by the edges are not only in the abnormal directions (22.5° and 67.5° in FIG. 36, 67.5°, 112.5° and 157.5° in FIG. 37) but also in the normal directions (45° in FIG. 36, and 90° and 135° in FIG. 37). The reflected diffraction lights in those directions are of substantially equal intensity because the intensities are proportional to the lengths of the edges.

In the prior art method, only the abnormal direction signals are used and the normal direction signals are not used. The erroneous detection due to the roundness can be eliminated by using both of the normal and abnormal direction signals. For example, even if the reflected diffraction light is generated in the 67.5° abnormal direction by the roundness shown in FIG. 36, the pattern is determined normal if the reflected diffraction light of substantially equal intensity as that in the 67.5° direction is generated in the 45° direction.

The above method which utilizes the reflected diffraction lights in the normal directions and the abnormal directions newly generated by the roundness can also be applied to the pattern 55 having right angle crossing edges and the pattern 56 having 45° crossing edges as shown in FIG. 38A and 38B, respectively. In FIGS. 36, 37, 38A and 38B, even if the pattern area and the non-pattern area are reversed, the same theory is applicable.

The second discrimination circuit thus directly utilizes the normal direction signals and the abnormal direction signals.

As described above, the second determination method includes the first and second discrimination circuit. In the first discrimination circuit, the defect pattern is detected if the sum of the four abnormal signals is larger than the threshold. In the second discrimination circuit, if the sum is smaller, the normality/abnormality is determined by other discrimination means using the predetermined discrimination threshold.

Figures 1A, 1B, 1C, 1D:
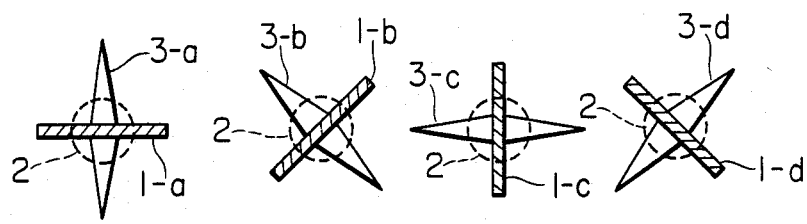
FIGS. 1A to 1E, 2A and 2B are diagrams used to explain the present invention.
Figure 1E:
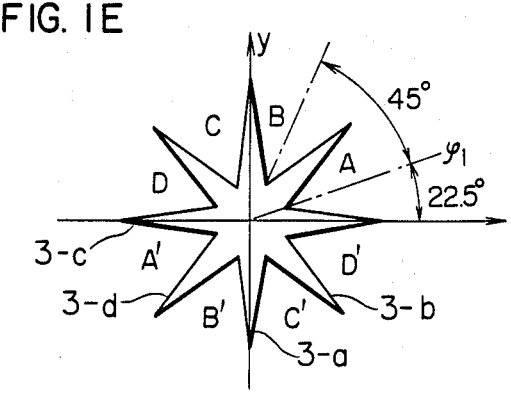
Figure 2A:
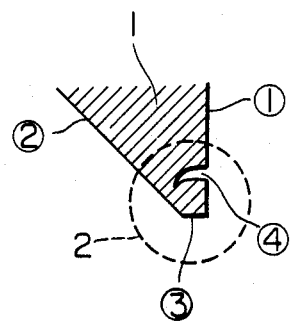
Figure 2B:
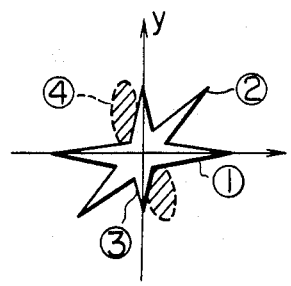
Figure 39:
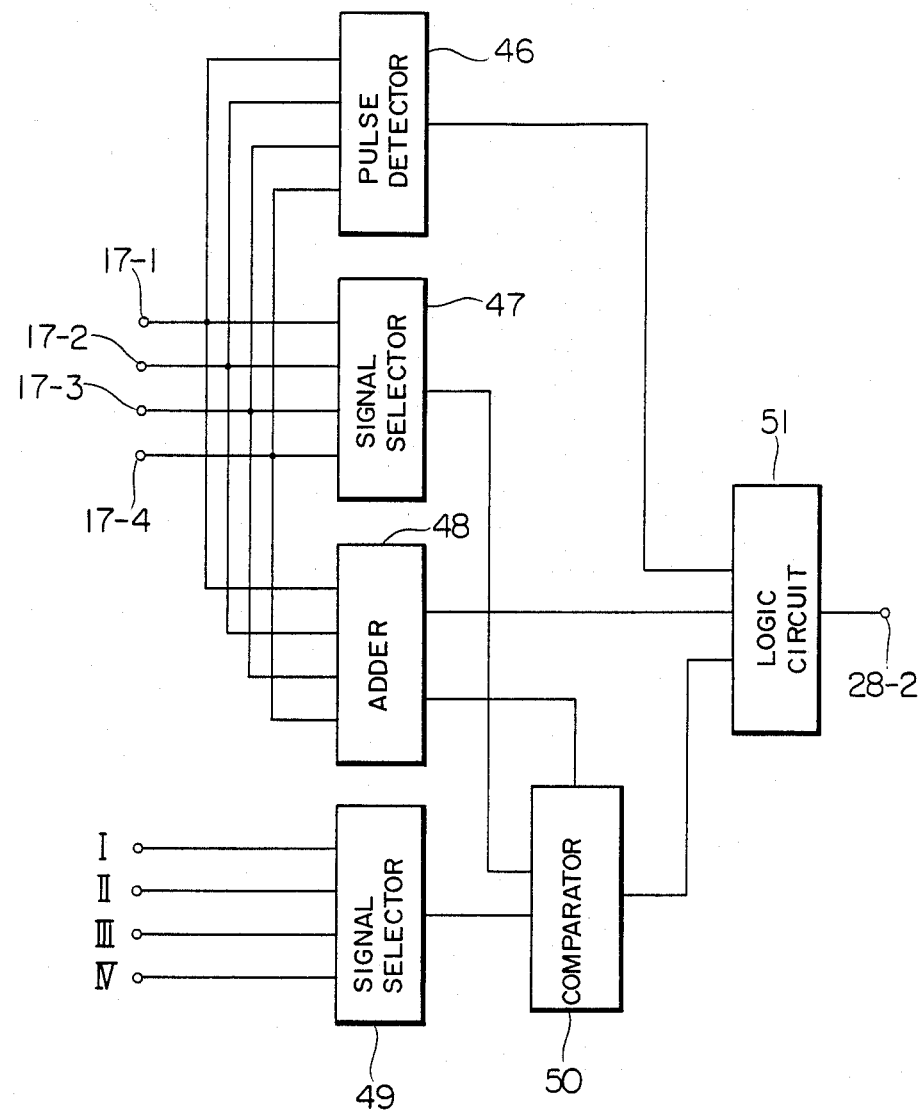
FIG. 39 is a block diagram of the other normal/abnormal discriminator.

The above method is explained with reference to FIG. 39. Applied to input terminals 17-1 to 17-4 are the outputs of the abnormal direction signal detection circuit of FIG. 9B. Numeral 46 denotes a pulse detector, numeral 47 denotes a first signal detector, numeral 48 denotes an adder, numeral 49 denotes a second signal selector, numeral 50 denotes a comparator and numeral 51 denotes a logic circuit. The abnormal direction signal is generated only when the reflected diffraction lights are generated toward the abnormal direction areas A-D and A'-D' (FIG. 1E) by the defect in the pattern, the deposition of the foreign material, the round corner or the disturbance in the edge, and no light is generated by the regularly oriented edges of the normal pattern. The level of the signal by the round corner is usually equal to or smaller than the level of the signal by the defect. Accordingly, if the sum of the four abnormal direction signals is larger than the threshold which is substantially equal to the level of the signal by the round corner, the pattern may be determined defective. The sum of the signals is produced by the adder 48.

Depending on the size and the shape of the defect, the level of the signal may be substantially equal to the level of the signal by the round corner. In this case, the signal by the defect and the signal by the round corner may be discriminated in the following manner. A signal which is next to the largest one of the four abnormal direction signals is selected by the first signal selector 47. It is designated by $e_{ab}$. A signal which is next to the smallest one of the four normal direction signals is selected by the second signal selector 49. It is designated by $e'$. The signal $e'$ is multiplied by a factor of $(1+\alpha)$ to produce a signal $e_{no}$ (where $\alpha$ is a real number between 0 and $\infty$). The signals $e_{ab}$ and $e_{no}$ are compared by the comparator 50 and the defect is determined if $e_{ab} > e_{no}$. The pulse detected by the pulse detector 46 passes through the logic circuit 51 to produce the defect signal only when the adder 48 or the comparator 50 detects the defect.

The reason for selecting the second largest signal in the abnormal direction and the second smallest signal in the normal direction is explained. In FIG. 36, the magnitudes of the reflected diffraction light in the 45° normal direction and the reflected diffraction lights in the 67.5° and 22.5° abnormal directions are substantially equal. While not shown in FIG. 36, because there exist high intensity 0° and 90° reflected diffraction lights and low intensity 135° reflected diffraction light, the 45° light is the second smallest one. In the abnormal direction, either one of 67.5° and 22.5° directions may be used (two other directions have low intensities) but the second largest one is used taking the pattern having 135° crossing edges into consideration. In FIG. 37, when the second smallest one of the four normal direction signals (high intensity 0° and 45° signals are not shown) is selected, the normal direction signal by the roundness is produced. If the second smallest one in the abnormal direction is selected, the reflected diffraction light by the roundness is produced.

FIGS. 40A and 40B collectively illustrate an example of an overall pattern defect inspection apparatus of the present invention and is intended to show how the circuitries explained heretofore are connected to each other. The defect signals at the terminals 28-1, 28-2 and 28-3 may be ANDed by an AND gate 181 so as to obtain a more accurate defect signal. Further explanation of FIG. 40 is omitted.

We claim:

1. A pattern defect inspection apparatus for inspecting a pattern defect by detecting reflected diffraction lights generated by scanning a surface of a semiconductor wafer, having a substantially straight edge pattern of an integrated circuit formed thereon, by means of a coherent light beam haing a predetermined spot size directed normally to the surface of the semiconductor wafer, in which the directions of the edges of said pattern include directions of 0°, 45°, 90° and 135° with respect to a reference direction, and two straight edges crossing each other provide a rounded corner due to fabrication limitations, said corner generating weaker reflected diffraction light than that from said straight edge, comprising:

> normal direction signal detection means including photo-detection means having wide light receiving areas arranged in a plurality of spatial areas in normal directions for converting the reflected diffraction lights generated from said pattern into electrical signals, said normal direction signal detection means providing a first group of normal direction signals when the photo-detector means receives reflected diffraction lights generated from said straight edge and a second group of normal direction signals when the photo-detector means receives reflected diffraction lights generated from said corner, said normal directions including directions of 0°, 45°, 90° and 135°;
>
> abnormal direction signal detection means including photo-detection means having wide light receiving areas arranged in a plurality of spatial areas in abnormal directions for converting the reflected diffraction lights generated from said pattern into electrical signals, said abnormal direction signal representative of the received reflected diffraction lights, said abnormal directions including directions of 22.5°, 67.5°, 112.5° and 157.5°;
>
> defect discrimination means for determining if the abnormal direction signal is due to a defect or not in accordance with the normal and abnormal direction signals from said abnormal direction signal detection means and said normal direction signal means, including means for classifying different patterns on the basis of said first and second groups of normal direction signals, as many normal/abnormal discriminators as the number of classes of the patterns for determining if the abnormal signals extracted by said abnormal signal detection means are due to a true defect or not, and activation means for selectively activating said normal/abnormal discriminators in accordance with the signal from the pattern classifying means.

2. A pattern defect inspection apparatus according to claim 1 wherein said abnormal direction signal detection means includes abnormal signal extraction means having floating threshold circuits for extracting said abnormal direction signal.

3. A pattern defect inspection apparatus according to claim 1, wherein each of said normal/abnormal discriminators includes comparator means and threshold setting means, wherein said comparator means compares said abnormal direction signal with the output of said threshold setting means activated by said activation means.

4. A pattern defect inspection apparatus for inspecting a pattern defect by detecting reflected diffraction lights generated by scanning a surface of a semiconductor wafer having a substantially straight edge pattern or an integrated circuit formed thereon by a coherent light beam having a predetermined spot size directed normally to the surface of the semiconductor wafer, in which the directions of said straight edge of said pattern include directions of 0°, 45°, 90° and 135° with respect to a reference direction, and two straight edges crossing each other provide a rounded corner due to fabrication limitations, said corner generating weaker reflected diffraction lights than those from said straight edge, comprising:

> normal direction signal detection means including a plurality of photo-detectors having wide light receiving areas arranged in a plurality of spatial areas in normal directions, for converting the reflected diffraction lights generated from said pattern and received by said photo-detectors into normal direction signals, said normal directions including directions of 0°, 45°, 90° and 135°;
>
> abnormal direction signal detection means including photo-detectors having wide light receiving areas arranged in a plurality of spatial areas in abnormal directions, for converting the reflected diffraction lights generated form said pattern and received said photo-detectors into abnormal signals, said abnormal directions including directions of 22.5°, 67.5°, 112.5° and 157.5°; and
>
> defect discrimination means for determining if the abnormal direction signal is due to a defect or not in accordance with the normal and abnormal direction signals from said abnormal direction signal detection means and said normal pattern detection means, including first compare means for comparing a sum of the abnormal direction signals with a threshold, first selection means for selecting a second signal of a predetermined magnitude order from the abnormal direction signals and second selection means for selecting a second signal of a predetermined magnitude order from the normal direction signals, and second compare means, including means for multiplying said second signal by a predetermined factor, for comparing said multiplied second signal with said first signal.

5. A pattern defect inspection apparatus for detecting a defect on a substantially straight edge pattern formed on a semiconductor wafer by scanning the semiconductor wafer by a coherent light beam, detecting reflected diffraction lights from said pattern, and detecting a change in the reflected diffraction lights due to disturbance in regularity of the pattern, in which the directions of said edge include 0°, 45°, 90° and 135° with respect to a reference direction, comprising:

> detectors for detecting normal direction signals from said pattern, said normal direction signals being generated by the reflected diffraction lights in a plurality of directions including directions of 0°, 45°, 90° and 135° in which the reflected diffraction light intensities are high because of said straight edge of said pattern;
>
> detectors for detecting abnormal direction signals from said pattern, said abnormal direction signals being generated by the reflected diffraction lights in a plurality of directions including directions of 22.5°, 67.5°, 112.5° and 157.5°, generated by a disturbance in the regularity of said pattern;
>
> pattern major-classifying signal generating means for major-classifying said pattern into one of a plurality of major classes in accordance with high level signals, generated by edges of the pattern, of the detected normal direction signals;
>
> pattern sub-classifying signal generating means for sub-classifying the major-classified normal patterns into a plurality of sub-classes in accordance with low level signals generated by a predetermined deviation from an ideal pattern, of the detected normal direction signals;

abnormal signal detection means including a floating threshold circuit for extracting abnormal signals from the detected abnormal direction signals;

a plurality of normal/abnormal discriminiators one for each of the classified patterns for determining if the detected abnormal signal is due to the defect in the pattern or not; and selection means for selecting said normal/abnormal discriminators suitable for the pattern in accordance with the major-classifying signal and the sub-classifying signal.

6. A pattern defect inspection apparatus according to claim 5 wherein said pattern major-classifying signal generating means includes means for generating pattern edge direction signals, a plurality of logic circuits for producing classifying signals one for each of the pattern classes and an inhibit circuit for inhibiting an erroneous output of the logic circuits.

7. A pattern defect inspection apparatus according to claim 5 wherein said pattern sub-classifying signal generating means includes means for producing a deviation direction signal based on low level normal signals generated by a deviation from an ideal pattern, logic circuits for generating sub-classifying signals one for each of the pattern classes, and an inhibit circuit for inhibiting an erroneous output of the logic circuits.

8. A pattern defect inspection apparatus for scanning a pattern formed on a semiconductor wafer by a converged coherent light beam and detecting reflected diffraction lights from the pattern by photo-detectors arranged in a plurality of directions in which the reflected diffraction lights are generated by a disturbance in regularity of the pattern, comprising:

a circuit for summing signals in all of said directions, comparing the sum with a threshold and detecting a pattern defect if the sum is larger than the threshold;

a circuit for selecting a signal or a predetermined magnitude order of the signals in the plurality of directions in which the reflected diffraction lights have high intensities because of the regularity of the pattern;

a circuit for selecting a signal of a predetermined magnitude order of the signals in the plurality of directions in which the reflected diffraction lights from the pattern are generated by the disturbance in the regularity of the pattern; and a circuit for processing said two selected signals and comparing the processed signals to determine the presence or absence of the defect.

9. A pattern defect inspection apparatus for scanning a pattern formed on a semiconductor wafer by a light beam of a predetermined spot size and detecting a defect on the pattern in accordance with reflected diffraction lights from the pattern, comprising:

first photo-detection means arranged in first plurality of directions in which the reflected diffraction lights are generated when a plurality of defect-free basic patterns are irradiated by said light beam, said first photo-detection means converting the reflected diffraction lights to first electrical signals;

second photo-detection means arranged in second plurality of directions in which the reflected diffraction lights are generated when a plurality of defective basic patterns are irradiated by said light beam, said second photo-detection means concerning the reflected diffraction lights to second electrical signals; and discrimination means for determining presence or absence of the defect on the pattern of the semiconductor wafer under inspection in accordance with the signals from said first and second photo-detection means, means for classifying the pattern on said semiconductor wafer to one of said basic patterns based on said first electrical signals and producing a select signal in accordance with the classification, means for detecting a defect signal representative of a defect size of the defective pattern based on said second electrical signals, second discrimination means one for each of the basic patterns for determining the presence or absence of the defect, means for setting thresholds corresponding to allowable defect sizes of the related basic patterns, means for comparing the defect signal with the thresholds, and selection means for selectively activating the second discrimination means corresponding to the selection signal.

10. A pattern defect inspection apparatus according to claim 11 further comprising means for determining the presence or absence of the defect in the pattern in accordance with a time interval between occurences of two or more sequential defect signals and directions of those signals in said second plurality of directions.

11. A pattern defect inspection apparatus for scanning a pattern formed on a semiconductor wafer by a light beam of a predetermined spot size and detecting a defect on the pattern in accordance with reflected diffraction lights from the pattern, comprising:

first photo-detection means arranged in first plurality of directions in which the reflected diffraction lights are generated when a plurality of defect-free basic patterns are irradiated by said light beam, said first photo-detection means converting the reflected diffraction lights to first electrical signals;

second photo-detection means arranged in second plurality of directions in which the reflected diffraction lights are generated when a plurality of defective basic patterns are irradiated by said light beam, said second photo-detection means concerning the reflected diffraction lights to second electrical signals; and discrimination means for determining presence or absence of the defect on the pattern of the semiconductor wafer under inspection in accordance with the signals from said first and second photo-detection means, means for summing all signals from said second photo-detection means, means for comparing the sum with a threshold and detecting the defect if the sum is larger than the threshold, means for detecting a signal of a predetermined magnitude order of the signals from said first photo-detection means when said sum is smaller than said threshold, means for selecting a signal of a predetermined magnitude order of the signals from said second photo-detection means, means for comparing said predetermined magnitude order signals, and means for detecting the defect if said predetermined magnitude order signal selected from the signals of said second photo-detection means is larger.

12. A circular pattern discriminator for use in a pattern defect inspection apparatus for detecting a defect in pattern including a circular pattern formed on a semiconductor wafer by scanning said wafer with a converged coherent light, comprising:

photo-detector means provided in each of a plurality of directions of reflected diffraction lights generated when a defectless circular pattern under scanning along a plurality of predetermined paths is irradiated at edge portions thereof, for providing a signal when there is present a reflected diffraction light, wherein said edge portion, if defectless, provides the diffraction light in a single direction, said single direction being determined by an angle of said edge portion, and wherein when said circular pattern is scanned along any one of said paths, occurrence order of first and second directions of consecutive two reflected diffraction lights occurring when said coherent light is first at a first edge portion and is then a second edge portion, respectively, of said circular pattern, are predetermined dependng upon the path; and means for determining whether the pattern under scanning is a circular pattern or not, said determination means including:

(a) means for storing value relating to a duration of time necessary for said coherent light to pass through said circular pattern;
(b) gating means each coupled to the associated one of said photo-detector means, each gating means gating (i.e., transmitting) the signal of the associated photo-detector means only when said associated photo-detector means alone detects the presence of the reflected diffraction light and the other photo-detector means do not; and
(c) means for storing the occurrence order of said first and second directions for each path, wherein said determining means determines a pattern under scan to be a circular pattern when consecutive two pulse signals transmitted from any two gating mens are one of said occurrence orders and are occurring within said value relating to said period of time.

13. A circular pattern discriminator according to claim 12, wherein said value is 90 percent of a duration of time required for the coherent light to scan the diameter of said circular pattern.

* * * * *